United States Patent
Artico et al.

(10) Patent No.: US 6,635,636 B1
(45) Date of Patent: Oct. 21, 2003

(54) SUBSTITUTED 6-BENZYL-4-OXOPYRIMIDINES, PROCESS FOR THEIR PREPARATION AND PHARMACEUTICAL COMPOSITIONS CONTAINING THEM

(75) Inventors: Marino Artico, Rome (IT); Paolo La Colla, Cagliari (IT)

(73) Assignee: Idenix Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/744,038

(22) PCT Filed: Jul. 19, 1999

(86) PCT No.: PCT/EP99/05134

§ 371 (c)(1),
(2), (4) Date: May 1, 2001

(87) PCT Pub. No.: WO00/03998

PCT Pub. Date: Jan. 27, 2000

(30) Foreign Application Priority Data

Jul. 17, 1998 (IT) .......................................... CA98A0015

(51) Int. Cl.⁷ .................... C07D 239/52; C07D 239/56; C07D 239/36; A61K 31/505
(52) U.S. Cl. ...................... 514/227.8; 544/321; 544/60; 544/123; 514/272; 514/235.8
(58) Field of Search .......................... 544/321, 60, 123; 514/272, 227.8, 235.8

(56) References Cited

U.S. PATENT DOCUMENTS

| | | | | |
|---|---|---|---|---|
| 3,956,302 A | * | 5/1976 | Hunter et al. ............. | 260/256.4 |
| 6,117,904 A | | 9/2000 | Murphy et al. ............. | 514/547 |
| 6,177,437 B1 | | 1/2001 | Wright ....................... | 514/274 |
| 6,376,504 B1 | | 4/2002 | Uckun et al. ............... | 514/274 |

FOREIGN PATENT DOCUMENTS

| WO | WO 91/18887 | 12/1991 |
|---|---|---|
| WO | WO 92/16201 | 10/1992 |
| WO | WO 00/03998 | 1/2000 |

OTHER PUBLICATIONS

CAS printout for Brown et al.*
CAS printout for Aroyan et al.*
CAS printout for Wagle et al.*
Nizi et al. Solid phase synthesis of 2,6–disubstituted pyrimidinones targeting HIV–1 reverse transcriptase, Tetrahedron Lett., 39: 3307–3310.*
CAS printout for Liu et al.*
CAS printout for Ife et al.*
CAS printout for Carter et al.*
Mai A. et al. J. Med. Chem. 1995, 38, 3258–3263.
Fenner H. et al. Arch. Pharm. 1978, 311:2, 115–125 (Abstract only; Chem Abst. vol. 88, No. 21; Abst. 152555q).
Botta, M. et al. Eur. J. Med. Chem. 1992, 27, 251.
Artico M. et al. Antiviral Chem. Chemother. 1993, 4, 361.
Tramontano E. et al. Microbiologica 1994, 17, 269.
Massa S. et al. Antiviral Chem. Chemother. 1995, 6, 8.
Mai A. et al. J. Med. Chem. 1995, 38, 3263.
Mai A. et al. J. Med. Chem. 1997, 40, 1447.
Mai A. et al. J. Med. Chem. 1999, 42, 619.
Sbardella G. et al. Antiviral Chem. Chemother. 2001, 12, 17.
Sbardella G. et al. Med. Chem. Res. 2000, 10, 30.
Costi R. et al. Antiviral Chem. Chemother. 2000, 11, 117.
Balzarini J. et al. Molecular Pharmacology 1993, 44, 694.
Masanori Baba et al. Antimicrobial Agents & Chemother. 1994, 38, 688.
Hiromichi Tanaka et al. J. Med. Chem. 1995, 38, 2860.

* cited by examiner

Primary Examiner—Richard L. Raymond
Assistant Examiner—Hong Liu
(74) Attorney, Agent, or Firm—King & Spalding LLP; Sherry M. Knowles, Esq.

(57) ABSTRACT

The invention concerns novel substituted 6-benzyl-4-oxopyrimidines and pharmaceutically acceptable salts thereof. These compounds inhibit reverse transcriptase encoded by human immunodeficiency virus (HIV), and are useful to prevent and treat HIV infection and acquired immune deficiency syndrome (AIDS). Pharmaceutical compositions containing the compounds and a method of use of the present compounds and other agents for the treatment of AIDS and viral infection by HIV are also envisaged.

49 Claims, No Drawings

SUBSTITUTED 6-BENZYL-4-OXOPYRIMIDINES, PROCESS FOR THEIR PREPARATION AND PHARMACEUTICAL COMPOSITIONS CONTAINING THEM

The present invention is concerned with compounds which inhibit the reverse transcriptase encoded by human immunodeficiency virus (HIV) or pharmaceutically acceptable salts thereof and are of value in the prevention of infection by HIV, the treatment of infection by HIV and the treatment of the resulting acquired immune deficiency syndrome (AIDS). It also relates to pharmaceutical compositions containing the compounds and to a method of use of the present compounds and other agents for the treatment of AIDS arid viral infection by HIV.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system.

Currently available drugs for AIDS therapy are divided into two groups: those that prevent infection of target cells [nucleoside (NRTIs) and non-nucleoside reverse transcriptase inhibitors (NNRTIs)], and those that prevent HIV-1-infected cells from yielding infectious viruses (protease inhibitors). Monotherapy with antiretroviral agents has shown limited effects, very likely due to the interplay of phenomena such as: high viral loads and multiplication rates of HIV, incomplete inhibition of viral replication and emergence of drug resistant mutants. For this reason, combination therapies with two or more drugs have been proposed for a more effective treatment of AIDS. Potent suppression of HIV replication over prolonged periods has been accomplished with regimens including reverse transcriptase and protease inhibitors, although on stopping therapies viraemia has rapidly reappeared. In the attempt to obtain better results, research is now focused on exploiting new targets and enhancing the activity of "old" drugs. Among the latter, NNRTs possibly endowed with better pharmacokinetic profiles, capability to inhibit clinically relevant mutants and, hopefully, to minimize HIV multiplication are being pursued.

Compounds of the present invention are dihydro-alkyloxy-benzyl-oxopyrimidines (DABOs) which potently inhibit HIV multiplication targeting reverse transcriptase without bioactivation.

BRIEF DESCRIPTION OF THE INVENTION

Novel compounds of formula A:

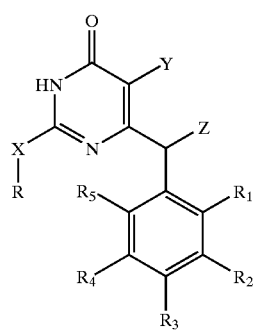

(A)

as herein defined, are disclosed. These compounds are useful in the inhibition of HIV reverse transcriptase, the prevention of infection by HIV, the treatment of infection by HIV and in the treatment of AIDS, either as compounds, pharmaceutically acceptable salts (when appropriate), pharmaceutical composition ingredients, whether or not in combination with other antivirals, anti-infectives, immunomodulators, antibiotics or vaccines. Methods of treating AIDS, methods of preventing infection by HIV, and methods of treating infection by HIV are also disclosed.

DETAILED DESCRIPTION OF THE INVENTION AND PREFERRED EMBODIMENTS

This invention is concerned with the compounds of formula A described below, combinations thereof, or pharmaceutically acceptable salts thereof, in the inhibition of HIV reverse transcriptase, the prevention or treatment of infection by HIV and in the treatment of the resulting acquired immune deficiency syndrome (AIDS). The compounds of this invention include those with structural formula A:

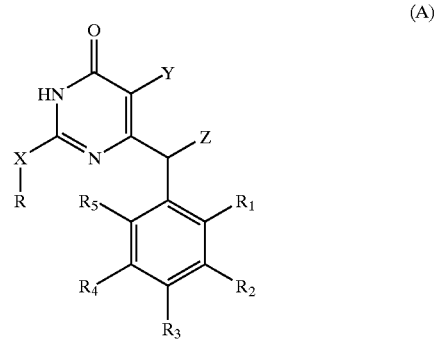

(A)

wherein:
  X is —O, —$CH_2$, —CHK (wherein K is —H, —$C_{1-4}$ alkyl, —$C_{3-6}$Cycloalkyl), —S, —NK (wherein K is —H, —$C_{1-4}$alkyl, —$C_{3-6}$cycloalkyl), -aryl, -arylalkyl;
  R is —H, —$C_{1-4}$alkyl (containing one or more of heteroatoms like O, S, N), —$C_{3-6}$ cycloalkyl (containing one or more of heteroatoms like O, S, N), -aryl, -arylakl, heterocycle;
  Y is —H, —$C_{1-4}$alkyl, —$C_{3-6}$cycloalkyl;
  Z is —H, —$C_{1-4}$alkyl, —$C_{3-6}$cycloalkyl;
  $R_1$ is —H, —$C_{1-4}$alkyl, -halogen, —$NO_2$, —OW (wherein W is —H, —$CH_3$, aryl), —SW (wherein W is —H, —$CH_3$, -aryl);
  $R_2$ is —H, —$C_{1-4}$alkyl, -halogen, —$NO_2$, (wherein W is —H, —$CH_3$, -aryl); —SW (wherein W is —H, —$CH_3$, -aryl);
  $R_3$ is —H, —$C_{1-4}$alkyl, -halogen, —$NO_2$, —OW (wherein W is —H, —$CH_3$, -aryl); —SW (wherein W is —H, —$CH_3$, -aryl)
  $R_4$ is —H, —$C_{1-4}$alkyl, -halogen, —$NO_2$, —OW (wherein W is —H, —$CH_3$, -aryl); —SW (wherein W is —H, —$CH_3$, -aryl)
  $R_5$ is —H, —$C_{1-4}$alkyl, -halogen, —$NO_2$, —OW (wherein W is —H, —$CH_3$, -aryl), —SW (wherein W is —H, —$CH_3$, -aryl);
  pharmaceutically acceptable salts or soluble derivatives thereof;
  preparation process of derivatives thereof;
  a method of preventing infection of HIV, or of treating infection by HIV or of treating AIDS, comprising administering to a mammal an effective amount of compounds claimed;

a pharmaceutical, composition useful for inhibiting HIV reverse transcriptase, comprising an effective amount of compounds claimed, and a pharmaceutically acceptable carrier;

a pharmaceutical composition useful for preventing or treating infection of HIV or for treating AIDS, comprising an effective amount of compounds claimed, and a pharmaceutically acceptable carrier.

The most preferred compounds of this invention are those of table 1.

The compounds of the present invention may have asymmetric centers and occur as racemates, racemic mixtures, individual diastereomers, or enantiomers, with all isomeric forms being included in the present invention.

When any variable occurs more than one time in any constituent or in formula A of this invention, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms; "Halogen" or "Hal" as used herein, means fluoro, chloro, bromo and iodo.

As used herein, with exceptions as noted, "aryl" is intended to mean any stable monocyclic, bicyclic or tricyclic carbon ring of up to 7 members in each ring, wherein at least one ring is aromatic. Examples of such aryl elements include phenyl, naphthyl, tetrahydronaphthyl, biphenyl.

The term heterocycle or heterocyclic, as used herein except where noted represents a stable 5- to 7-membered monocyclic or stable 8- to 11-membered bicyclic heterocyclic ring which is either saturated or unsaturated, and which consists of carbon atoms and from one to three heteroatoms selected from the group consisting of N, O and S; and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

The pharmaceutically-acceptable salts of the novel compounds of this invention that are capable of salt formation (in the form of water- or oil-soluble or dispersible products) include the conventional non-toxic salts or the quaternary ammonium salts of these compounds, which are formed, e.g.; from inorganic or organic acids or bases.

In preferred embodiments, a compound of the present invention is administered in combination or alternation with AZT, D4T, FTC (2',3'-dideoxy-3'-thia-5-fluorocytidine); 3TC (Epivir, Glaxo Wellcome, Inc.), AZDU (3'-Azido-2',3'-dideoxyuridine); 141W94 (amprenavir, GlaxoWellcome, Inc.); Viramune (nevirapine), Rescriptor (delavirdine); or DMP-266 (efavirenz). Other examples of antiviral agents that can be used in combination or alternation with the compounds disclosed herein for HIV therapy include DDI, DDC, Delaviridine, β-LddA, β-L-3'-azido-d5FC, carbovir, acyclovir, interferon, stavudine, CS-92 (3'-azido-2',3'-dideoxy-5-methyl-cytidine), 3'-azido nucleosides, and β-D-dioxolane nucleosides such as β-D-dioxolanylguanine (DXG), β-D-dioxolanyl-2,6-diaminopurine (DAPD), and β-D-dioxolanyl-6-chloropurine (ACP).

Preferred protease inhibitors include indinavir ({1(1,S,2R),5(S)]-2,3,5-trideoxy-N-(2,3-dihydro-2-hydroxy-1H-inden-1-yl)-5-[2-[[(1,1-dimethylethyl)amino]carbonyl]-4-(3-pyridinylmethyl)-1-piperazinyl]-2-(phenylmethyl)-D-erythro-pentoamide sulfate; Merck), nelfinavir (Agouron), ritonavir (Abbot), and saquinavir (Invirase; Roche).

Nonlimiting examples of other compounds that can be administered in combination or alternation with the compounds of the present invention to augment the properties of the drug on administration include abacavir: (1S,4R)-4-[2-amino-4-cyclopropyl-amino)-9H-purin-9-yl]-2-cyclopentene-1-methanol succinate (1592U89, a carbovir analog; Glaxo Wellcome); zidovudine: AZT, 3'-azido-3'-deoxythymidine (Glaxo Wellcome); BILA 1906: N-{1S-[[[3-[2S-{(1,1-dimethylethyl)amino]carbonyl}-4R-]3-pyridinylmethyl)thio]-1-piperidinyl]-2R-hydroxy-1S-(phenylmethyl)propyl]amino]carbonyl}-2-methylpropyl}-2-quinolinecarboxamide (Bio Mega/Boehringer-Ingelheim); BILA 2185: N-(1,1-dimethylethyl)-1-[2S-[[2-2,6-dimethylphenoxy)-1-oxoethyl]amino]-2R-hydroxy-4-phenylbutyl]4R-pyridinylthio)-2-piperidinecarboxamide (Bio Mega/Boehringer-Ingelheim); BM+51.0836:triazoloisoindolinone derivative; BMS 186, 318: aminodiol derivative HIV-1 protease inhibitor (Bristol-Myers-Squibb); d4API: 9-[2,5-dihydro-5-(phosphonomethoxy)-2-furanel]adenine (Gilead); stavudine: d4T, 2',3'-didehydro-3'-deoxythymidine (Bristol-Myers-Squibb); efavirenz: DMP-266, a 1,4-dihydro-2H-3,1-benzoxazin-2-one; HBY097: S-4-isopropoxycabonyl-6-methoxy-3-(methylthio-methyl)-3,4-dihydroquinoxalin-2 (1H)-thione; HEPT: 1-[(2-hydroxyethoxy)methyl]6-(phenylthio)thymine; KNI-272: (2S,3S)-3-amino-2-hydroxy-4-phenylbutyric acid-containing tripeptide; L-697, 593; 5-ethyl-6-methyl-3-(2-phthalimido-ethyl)pyridin-2 (1H)-one; L-735,524: hydroxy-aminopentane amide HIV-1 protease inhibitor (Merck); L-697,661: 3-{[(-4,7-dichloro-1,3-benzoxazol-2-yl)methyl]amino}-5-ethyl-6-methylpyridin-2(1H)-one; L-FDDC: (−)-β-L-5-fluoro-2',3'-dideoxycytidine; L-FDOC: (−)-β-L-5-fluoro-dioxolane cytosine; 6-benzyl-1-ethoxymethyl-5-isopropyluracil (I-EBU; Triangle/Mitsubishi); nevirapine: 11-cyclopropyl-5,11-dihydro-4-methyl-6H-dipyridol[3,2-b:2',3'-e]diazepin-6-one (Boehringer-Ingelheim); PFA: phosphonoformate (foscarnet; Astra); PMEA: 9-(2-phosphonylmethoxyethyl) adenine (Gilead); PMPA: (R)-9-(2-phosphonyl-methoxypropyl)adenine (Gilead); Ro 31-8959: hydroxyth-ethylamine derivative HIV-1 protease inhibitor (Roche); RPI-3121: peptidyl protease inhibitor, 1-[(3s)-3-(n-alpha-benzyloxycarbonyl)-1-asparginyl)-amino-2-hydroxy-4-phenylbutyryl]-n-tert-butyl-1-proline amide; 2720: 6-chloro-3,3-dimethyl-4-(isopropenyloxycarbonyl)-3,4-dihydro-quinoxalin-2(1H)thione; SC-52151: hydroxyethy-lurea isostere protease inhibitor (Searle); SC-55389A: hydroxyethyl-urea isostere protease inhibitor (Searle); TIBO R82150: (+)-(5S)-4,5,6,7-tetrahydro-5-methyl-6-(3-methyl-2-butenyl)imidazo[4,5,1-jk][1,4]-benzodiazepin-2(1H)-thione (Janssen); TIBO 82913: (+)-(5S)-4,5,6,7,-tetrahydro-9-chloro-5-methyl-6-(3-methyl-2-butenyl)imidazo[4,5,jk]-[1,4]benzodiazepin-2(1H)-thione (Janssen); TSAO-m3T: [2',5'-bis-O-(tert-butyldimethylsilyl)-3'-spiro-5'-(4'-amino-1',2'-oxathiole-2',2'-dioxide)]-β-D-pentofuranosyl-N3-methylthymine; U90152: 1-[3-[(1-methylethyl)-amino]2-pyridinyl]-4-[[5-[(methylsulphonyl)-amino]-1H-indol-2yl] carbonyl]piperazine; UC: thiocarboxanilide derivatives (Uniroyal); UC-781=N-[4-chloro-3-(3-methyl-2-butenyloxy)phenyl]-2-methyl-3-furancarbothioamide; UC-82=N-[4-chloro-3-(3-methyl-2-butenyloxy)phenyl]-2-methyl-3-thiophenecarbothioamide; VB 11,328: hydroxy-ethylsulphonamide protease inhibitor (Vertex); VX-478: amprenavir, 141W94, hydroxyethylsulphonamide protease inhibitor (Vertex/Glaxo Wellcome); XM 323: cyclic urea protease inhibitor (Dupont Merck), delaviridine (Pharmacia Upjohn), famciclovir, gancyclovir, and penciclovir. In another embodiment, a compound of the present invention is administered in combination with LG1350, which has the following structure.

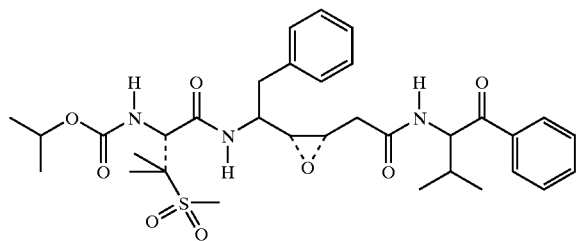

Preparation Of Methyl Arylacetylalkylacetates
SCHEME A

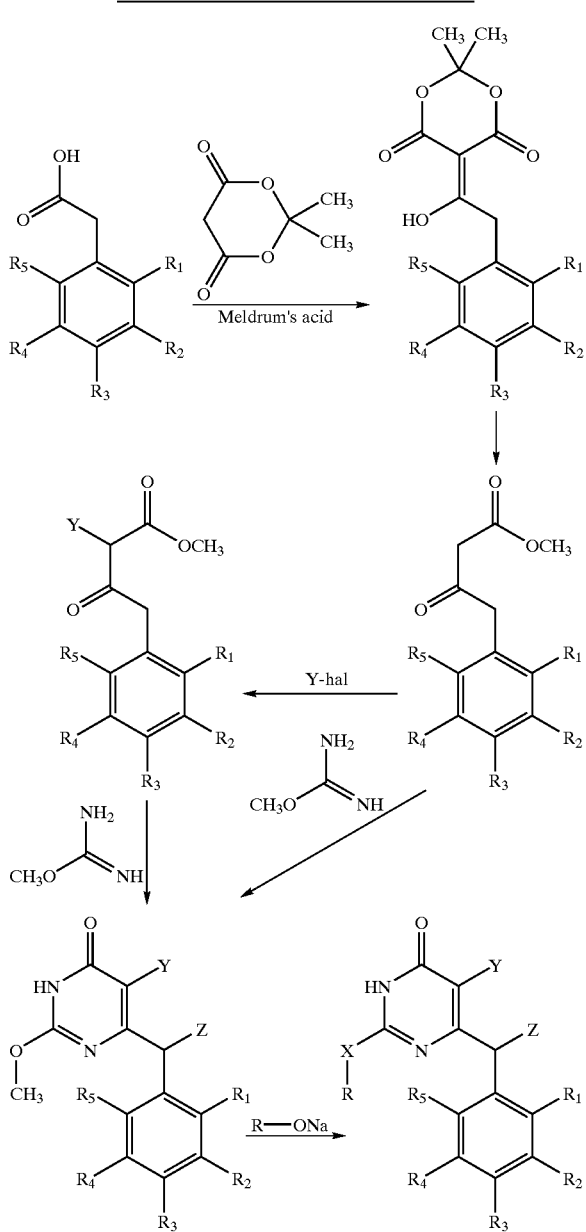

Anhydrous pyridine (400 mmoles, 32.5 ml) was added with stirring under nitrogen atmosphere into an ice-cooled solution of 2,2-dimethyl-1,3-dioxane-4,6-dione (Meldrum's acid) (165 mmoles, 23.75 g) in anhydrous dichloromethane (50 ml). The resulting solution was treated, over a 2 h period at 0° C. under nitrogen atmosphere, with a solution of crude arylacetyl chloride in anhydrous dichloromethane (50 ml). Arylacetyl chloride was prepared before use by refluxing the proper arylacetic acid (43.2 mmoles) with thionyl chloride (21.3 ml) under nitrogen atmosphere for 2 h. Then, the mixture was stirred for 2 h at room temperature, poured into crushed ice and treated with 2N HCl (100 ml). The organic layer was separated and the aqueous solution was extracted twice with dichloromethane (25 ml). The organic phase and the extracts were combined, washed with brine, dried and evaporated. The solid residue was dissolved in anhydrous methanol (250 ml) and the solution was refluxed for 20 h. After cooling, metal sodium (0.16 g-atoms, 3.68 g) was carefully added and the mixture was stirred until dissolution was complete. Alkyl halide (160 mmoles) was dropped into the solution and the resulting mixture was heated at reflux for 4–12 h. After cooling, the solvent was removed and the residue treated with water (200 ml) and extracted with chloroform (3×100 ml). The organic layer was washed with brine (2×100 ml), dried and evaporated to give the desired compound, which was purified by passing through a silica gel column (chloroform as eluent).

In the above reaction, arylacetic acid (Scheme "A") or arylacetyl chloride can be replaced with the corresponding 1-arylacetylimidazolide (Scheme "B") or with arylacetylethoxycarbonylanhydride, whereas the Meldrum's acid can be replaced with ethyl acetylacetate, ethyl alkylmalonate or ethyl alkylmalonate potassium salt, to give the proper ethyl arylacetylalkylacetates in high yields.

Preparation of Compounds (I) With
X=O (Scheme A)

The proper methyl arylacetylalkylacetate (10 mmoles) in methanol (50 ml) was added to a well-stirred suspension of O-methylisourea hydrogen sulphate (15 mmoles, 2.58 g) and calcium hydroxide (16 mmoles, 1.18 g) in water (50 ml). The resulting mixture was stirred at room temperature for 72 h, then concentrated, made acid (pH 5) with 0.5N acetic acid and extracted with ethyl acetate (3×50 ml). The combined organic extracts were washed with brine (100 ml), dried and evaporated to dryness. The residue was purified by crystallization from the proper solvent yielding pure 5-alkyl-6-benzyl-3,4-dihydro-2-methoxypyrimidin-4-one. This compound was then refluxed with the proper potassium alkoxide (100 mmoles of potassium metal in 20–30 ml of alcohol freshly distilled on sodium metal) under nitrogen atmosphere until starting material disappeared at the TLC control. After cooling, the mixture was concentrated, made acid (pH 5) with 0.5N acetic acid and extracted with ethyl acetate (3×50 ml). The combined extracts were washed once with brine (100 ml), dried and evaporated to give the required 2-alkoxy-5-alkyl-6-benzyl-3,4-dihydropyrimidin-4-one derivative, which was recrystallized from a suitable solvent or purified by column chromatography (silica gel; ethyl acetate:chloroform 1:1). Physical and chemical data of representative compounds of the invention are reported in table 1; cytotoxicity and anti-HIV-1 activity data are reported in table 2.

Preparation of Compounds (I) with X=S

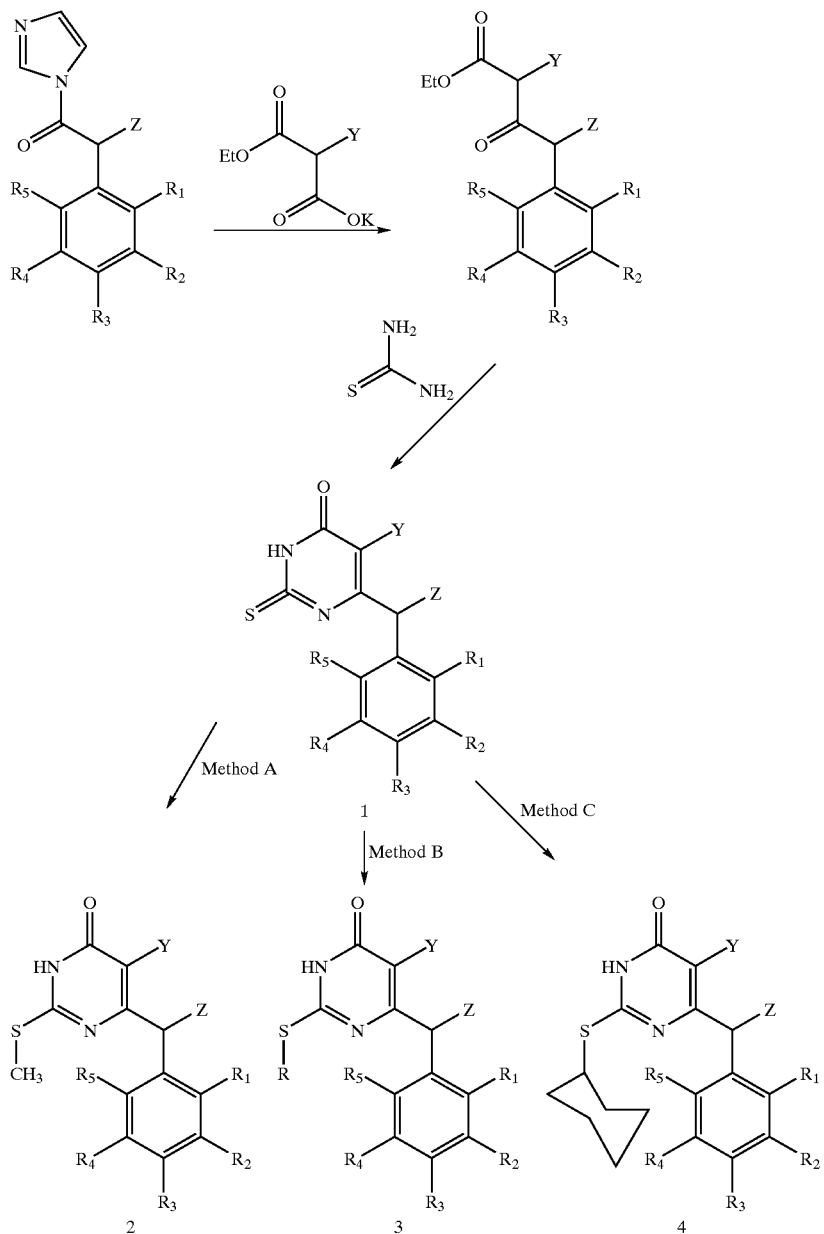

The proper ethyl arylacetylalkylacetate (31.5 mmole as successively added to a stirred solution of sodium metal (0.063 g-atoms) in 50 mL of absolute ethanol (50 ml) thiourea (43 mmoles). The mixture was heated while stirring at reflux for 5 h. After cooling, the solvent was distilled in vacuo at 40–50° C. until dryness and the residue was dissolved in water (200 mL) and made acid (pH 5) with 0.5N acetic acid. The resulting precipitate (the crude 2-thiouracil derivative) was filtered under reduced pressure, washed with diethyl ether, vacuum dried at 80° C. for 12 h and then crystallized from the proper solvent.

Then, according to method A, iodomethane (8 mmoles, 1.13 g) was added to a suspension containing the proper 2-thiouracil derivative (4 mmoles) in anhydrous N,N-dimethylformamide (2 ml), and the resulting mixture was stirred at room temperature until the starting material disappeared at the TLC control (silica gel; n-hexane: ethyl acetate:methanol 12:3:1). Then the reaction content was poured on cold water (100 mL) and extracted with ethyl acetate (3×50 ml). The organic layers were collected, washed with a sodium thiosulfate solution (100 ml), brine (3×50 ml), dried and evaporated to furnish the crude 5-alkyl-6-benzyl-3,4-dihydro-2-methylthiopyrimidin-4-one (2) as a solid purified by crystallization.

Alternatively, according to methods B and C, potassium carbonate (4.2 mmoles) and the proper alkyl halide (4.4 mmoles) were added to a suspension containing 2-thiouracil derivative (4 mmoles) in anhydrous N,N- dimethylformamide (2 ml). The resulting mixture was stirred at room temperature (method B) or at 80° C. (method C) until starting material disappeared at the TLC control (silica gel; n-hexane:ethyl acetate:methanol 12:3:1). Then the reaction content was poured on cold water (200 mL), made acid (pH 5) with 0.5N acetic acid and extracted with ethyl acetate (3×50 ml). The organic layers were collected, washed with a sodium thiosulfate solution (100 ml), brine (100 ml), dried and evaporated to furnish 5-alkyl-6-benzyl-3,4-dihydro-2-methylthiopyrimidin-4-ones (3) and (4) as crude material which was then purified by column chromatography on silica gel (eluent: n-hexane:ethyl acetate:methanol 12:3:1) followed by crystallization. Physical and chemical data of representative compounds of the invention are reported in table 1. Cytotoxicity and anti-HIV-1 activity in vitro are reported in table 2.

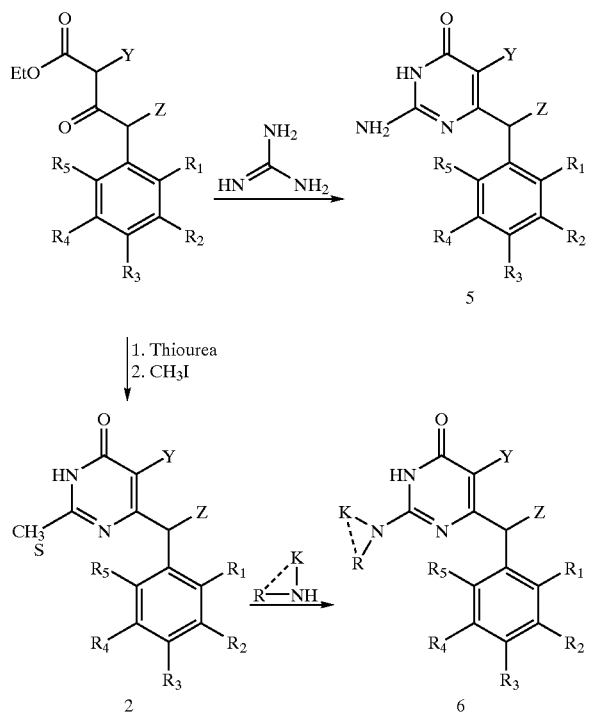

Preparation Of Compounds (I) With X = NK
SCHEME C

Title derivatives were prepared according to the procedure described for the synthesis of compounds with X=S (I), using ethyl arylacetylalkylacetates and guanidine [2-amino-6-benzylpyrimidin-4-ones (5)] as starting materials. 2-Alkylaminoderivatives (6) were synthesized by heating the previously reported 5-alkyl-6-benzyl-3,4-dihydro-2-methylthio pyrimidin-4-ones with 20–30 ml of proper amine in a sealed tube at 170° C. for 24 h. Physical and chemical data of some compounds (6) are reported in table 1. Cytotoxicity and anti-HIV-1 activity in vitro are reported in table 2. The compounds of the present invention are useful in the inhibition of HIV reverse transcriptase, the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

The compounds of this invention are also useful in the preparation and execution of screening for antiviral compounds. For example, the compounds of this invention are useful for isolating enzyme mutants, which are excellent screening tools for more powerful antiviral compounds. Furthermore, the compounds of this invention are useful in establishing or determining the binding site of other antiviral to HIV reverse transcriptase e.g., by competitive inhibition. Thus the compounds of this invention are commercial products to be sold for these purposes. For inhibition of HIV reverse transcriptase, the prevention or treatment of infection by HIV and the treatment of AIDS or ARC, the compounds of the present invention may be administered orally, parenterally (including subcutaneous injections, intravenous, intramuscular, intrasternal injection or infusion techniques), by inhalation spray, or rectally, in dosage unit formulations containing conventional non toxic pharmaceutically-acceptable carriers, adjuvants and vehicles. Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically effective amount of a compound of the present invention. These pharmaceutical compositions may be in the form of orally administrable suspensions or tablets; nasal sprays: sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient; such as cocoa buffer, synthetic glyceride, esters or polyethylene glycols, which are solid at ordinary temperatures, but liquidity and/or dissolve in the rectal cavity to release the drug.

The compounds of this invention can be administered orally to humans in a dosage range of 1 to 75 mg/kg body weight. One preferred dosage range is 1 to 50 mg/kg body weight orally. Another preferred dosage range is 5 to 75 mg/kg body weight orally. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV reverse transcriptase inhibitor compounds with one or more agents useful in the treatment of AIDS. The compounds of this invention can be administered in combination with other compounds that are HIV reverse transcriptase inhibitors, and/or with compounds that are HIV protease inhibitors. When used in a combination treatment with compounds of the instant invention, dosage levels of HIV protease inhibitors of the order of 1 to 25 or 50 grams-per-day are useful in the treatment or prevention of the above-indicated conditions, with oral doses two-to-five time higher. For example, infection by HIV is effectively treated by the administration of from 5 to 25 milligrams of the HIV protease inhibitor per kilogram of body weight from one to three times per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. Dosages of HIV reverse transcriptase inhibitors, when used in a combination treatment with compounds of the present invention, are comparable to those dosages specified above for the present compounds. It will be understood that the scope of combinations of the compounds of this invention with AIDS antivirals includes any combination with any pharmaceutical composition useful for the treatment of AIDS.

ANTIVIRAL ASSAY PROCEDURES

Compounds. Compounds were solubilized in DMSO at 200 mM and then diluted into culture medium.

Cells and viruses. MT-4, C8166, H9/IIIB and CEM cells were grown at 37° C. in a 5% $CO_2$ atmosphere in RPMI 1640 medium, supplemented with 10% fetal calf serum (FCS), 100 UI/mL penicillin and 100 μg/mL streptomycin. Cell cultures were checked periodically for the absence of mycoplasma contamination with a MycoTect Kit (Gibco). Human immunodeficiency virus type-1 (HIV-1, $III_B$ strain) was obtained from supernatants of persistently infected H9/$III_B$ cells. HIV-1 stock solution had a titres of $4.5 \times 10^6$ 50% cell culture infectious dose ($CCID_{50}$)/ml.

HIV titration. Titration of HIV was performed in C8166 cells by the standard limiting dilution method (dilution 1:2, four replica wells per dilution) in 96-well plates. The infectious virus titre was determined by light microscope scoring of cytopathicity after 4 days of incubation and the virus titres were expressed as $CCID_{50}$/mL.

Anti-HIV assays. Activity of the compounds against HIV-1 and HIV-2 multiplication in acutely infected cells was based on the inhibition of virus-induced cytopathicity in MT-4 and C8166 cells, respectively. Briefly, 50 μL of culture medium containing $1 \times 10^4$ cells were added to each well of flat-bottom microtiter trays containing 50 μl of culture medium with or without various concentrations of the test compounds. Then 20 μL of an HIV suspension containing 100 $CCID_{50}$ were added. After a 4-day incubation at 37° C., the number of viable cells was determined by the 3-(4,5-dimethylthiazol-1-yl)-2,5-diphenyltetrazolium bromide (MTT) method. Cytotoxicity of the compounds was evaluated in parallel with their antiviral activity. It was based on the viability of mock-infected cells, as monitored by the MTT method.

RT assays. Assays were performed as follows. Briefly, purified rRT was assayed for its RNA-dependent polymerase-associated activity in a 50 μL volume containing: 50 mM TrisHCl (pH 7.8). 80 mM KCl1, 6 mM MgCl2, 1 mM DTT. 0.1 mg/mL BSA, 0.3 $OD_{260}$ unit/mL template:primer [poly(rC)-oligo(dG)12–18] and 10 μM [$^3$H]dGTP (1 Ci/mmol). After incubation for 30 min at 37° C., the samples were spotted on glass fiber filters (Whatman GF/A), and the acid-insoluble radioactivity was determined.

EXAMPLES

2-Cyclopentylthio-6-(2,6-difluorophenylmethyl)-3,4-dihydrogyrimidin-4-(3H)-one (MC867)

A mixture of 6-(2,6-difluorophenylmethyl)-1,2,3,4-tetrahydro-2-thiopyrimidin-4(3H)-one (0.16 g, 0.65 mmol; prepared as reported in scheme B), cyclopentyl bromide (0.11 g, 0.08 mL., 0.71 mmol) and potassium carbonate (0.09 g, 0.65 mmol) in 1 mL of anhydrous DMF was stirred at room temperature for 24 h. After treatment with cold water (200 mL), the solution was extracted with ethyl acetate (3×50 mL). The organic layers were collected, washed with brine (3×50 mL), dried and evaporated to furnish crude MC867, which was purified by chromatography on silica gel column (eluent: n-hexane/ethyl acetate/methanol 12/3/1).

Yield (%): 45; mp (° C.): 168–169; recrystallization solvent: cyclohexane; formula (molecula-weight): $C_{16}H_{16}F_2N_2OS$ (322.37).

2-Cyclopenlythio-6-(2,6-diflurophenymethyl)-3,4-dihydro-5-methylpyrimidin-4-(3H)-one (MC922)

The synthesis of MC922 was accomplished according to the above reported procedure starting from 6-(2,6-difluorophenylmethyl)-5-methyl-1,2,3,4-tetrahydro-2-thiopyrimidin-4-(3H)-one (see scheme B).

Yield (%): 54; mp (° C.): 192–193; recrystallization solvent: cyclohexane; formula (molecular weight): $C_{17}H_{18}F_2N_2OS$ (336.40).

2-Cyclopentylthio-6-[1-(2,6-difluorophenyl)ethyl]-3,4-dihydropyrimidin-4-(3H)-one (MC1008)

The synthesis of MC1008 was accomplished according to the above reported procedure starting from 6-[1-(2,6-difluorophenyl)ethyl]-1,2,3,4-tetrahydro-2-thiopyrimidin-4-(3H)-one (see scheme B).

Yield (%): 54; mp (° C.): 165.5–166.5; recrystallization solvent: cyclohexane; formula (molecular weight): $C_{17}H_{18}F_2N_2OS$ (336.40).

2-Cyclopentylthio-6-[1-(2,6-difluorophenyl)ethyl]-3,4-dihydro-5-methylpyrimidin4(3H)-one (MC1047)

The synthesis of MC1047 was accomplished according to the above reported procedure, starting from 6-[1-(2,6- difluorophenyl)ethyl]-5-methyl-1,2,3,4-tetrahydro-2-thiopyrimidin-4(3H)-one (see scheme B).

Yield (%): 60; mp (° C.): 196–197; recrystallization solvent: cyclohexane; formula (molecular weight): $C_{18}H_{20}F_2N_2OS$ (350.43).

6-(2,6-Difluorophenymethyl)-3,4-dihydro-2-(methylthiomethyl)thiopyrimidin-4-(3H)-one (MC1161)

The synthesis of MC1161 was accomplished according to the above reported procedures, starting from 6-(2,6-difluorophenylmethyl)-1,2,3,4-tetrahydro-2-thiopyrimidin-4(3H)-one (see scheme B) and chloromethyl methyl sulfide.

Yield (%): 72; mp (° C.): 159–160; recrystallization solvent: benzene/cyclohexane; formula (molecular weight): $C_{13}H_{12}F_2N_2OS_2$ (314.37).

6-(2,6-Difluorophenylmethyl)-3,4-dihydro-5-methyl-2-(methylthiomethylthiopyrimidin-4(3H)-one (MC1162)

The synthesis of MC1162 was accomplished according to the above reported procedure, starting from 6-(2,6-difluorophenylmethyl)-5-methyl-1,2,3,4-tetrahydro-2-thiopyrimidin 4(3H)-one (see scheme B) and chloromethyl methyl sulfide.

Yield (%): 70; mp (° C.): 183–184; recrystallization solvent: benzene/cyclohexane; formula (molecular weight): $C_{14}H_{14}F_2N_2OS_2$ (328.39).

6-(2,6-Difluorophenylmethyl)-3,4-dihydro-5-(1-methylethyl)-2-(methylthiomethyl)) thiopyrimidin-4-(3H)-one MC1145)

The synthesis of MC1145 was accomplished according to the above reported procedure, starting from 6-(2,6-difluorophenylmethyl)-5-(1-methylethyl)-1,2,3,4-tetrahydro-2-thiopyrimidin-4(3H)-one (see scheme B) and chloromethyl methyl sulfide.

Yield (%): 62; mp (° C.): 158.5–160; recrystallization solvent: cyclohexane; formula (molecular weight): $C_{16}H_{18}F_2N_2OS_2$ (356.45).

2-Cyclopenltylamino-6-(2,6-difluorophenylmethyl)-3,4-dihydropyrimidin-4-(3H)-one (MC1022)

Cyclopentylamine (10 mL) was heated while stirring with 6-(2,6-difluorophenylmethyl)-3,4-dihydro-2-methylthiopyrimidin-4(3H)-one (0.30 g, 1.12 mmol; prepared as reported in scheme B or C) in a sealed tube at 160° C. for 10 h. After cooling, the mixture was diluted with water (200 mL) and extracted with ethyl acetate (3×50 mL). The organic layers were collected, washed with brine (3×50 mL), dried and evaporated to furnish crude MC1022, which was purified by chromatography on silica get column (eluent: ethyl acetate/chloroform 1/1).

Yield (%): 74: mp (° C.):—(oil); formula (molecular weight): $C_{16}H_{17}F_2N_3O$ (305.33).

2-Cyclopentylamino-6-(2,6-difluorophenylmethyl)-3,4-dihydro-5-methylpyrimidin-4-one (MC1050)

The synthesis of MC1050 was accomplished according to the above reported procedure, starting from 6-(2,6-difluorophenylmethyl)-3,4-dihydro-5-methyl-2-methylthiopyrimidin-4(3H)-one (see scheme B or C).

Yield (%): 60:. mp (° C.): 115–117; recrystallization solvent: n-hexane/cyclohexane; formula (molecular weight): $C_{17}H_{19}F_2N_3O$ (319.35).

2-Cyclopentylamino-6-[1-(2,6-difluorophenyl)ethyl]-3,4-dihydropyrimidin-4-(3H)-one (MC1048)

The synthesis of MC1048 was accomplished according to the above reported procedure, starting from 6-[1-(2,6-difluorophenyl)ethyl]-3,4-dihydro-2-methylthiopyrimidin-4(3H)-one (see scheme B or C).

Yield (%): 48: mp (° C.):—(oil); formula (molecular weight) $C_{17}H_{19}F_2N_3O$ (319.35).

2-Cyclopentylamino-6-[1-(2,6-difluorophenylethyl]-3,4-dihydro-5-methylpyrimidin-4-(3H)-one (MC1129)

The synthesis of MC1129 was accomplished according to the above reported procedure, starting from 6-[1-(2,6-difluorophenyl)ethyl]-3,4-dihydro-5-methyl-2-methylthiopyrimidin-4(3H)-one (see scheme B or C).

Yield (%): 38; mp (° C.):—(oil); formula (molecular weight): $C_{18}H_{21}F_2N_3O$ (333.38).

6-(2,6-Difluorophenylmethyl)-3,4-dihydro-2-(4-thiomorpholin-1-yl)pyrimidin-4-(3H)-one (MC1193)

The synthesis of MC1193 was accomplished according to the above reported procedure, starting from thiomorpholine and 6-(2,6-difluorophenylmethyl)-3,4-dihydro-2-methylthiopyrimidin-4(3H)-one (see scheme B or C).

Yield (%) 78, mp (° C.): 233–234; recrystallization solvent: acetonitrile; formula (molecular weight): $C_{15}H_{15}F_2N_3OS$ (323.36).

6-(2,6-Difluorophenylmethyl)-3,4-dihydro-2-N,N-dimethylaminopyrimidin-4-(3H)-one (MC1182)

To a stirred solution of sodium metal (0.14 g, 6.3 mg-atoms) in absolute ethanol (50 mL) 1,1-dimethylguanidine sulfate (1.17 g, 4.3 mmol) and ethyl 4-(2,6-difluorophenyl)acetylacetate (0.76 g, 3.15 mmol) were successively added. The mixture was heated while stirring at reflux for 8 h. After cooling, the solvent was distilled in vacuo at 40–50° C. until dryness and the residue was dissolved in water (200 mL) and made acid (pH 5) with 0.5N acetic acid. The resulting precipitate (the crude isocytosine derivative) was filtered under reduced pressure, washed with diethyl ether, vacuum dried at 80° C. for 12 h and then crystallized from benzene/cyclohexane (see scheme C starting from ethyl 4-(2,6-difluorophenyl) acetylacetate and replacing guanidine hydrochloride with 1,1-dimethylguanidine sulfate).

Yield (%): 88; mp (° C.): 210–211: recrystallization solvent: benzene/cyclohexane; formula (molecular weight): $C_{13}H_{13}F_2N_3O$ (265.26).

TABLE 1

Physical and Chemical Data of MC Compounds

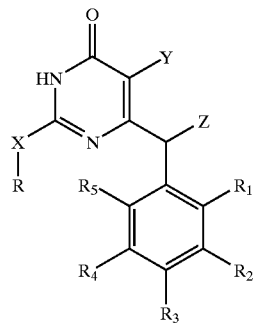

| Compd. | X | Y | Z | R | R¹ | R² | R³ | R⁴ | R⁵ | m.p., °C |
|---|---|---|---|---|---|---|---|---|---|---|
| MC 507 | O | H | H | 2,5-Me$_2$-c-hex | H | H | H | H | H | 130–132 |
| MC 508 | O | H | H | 4,5-Me$_2$-c-hex | H | H | H | H | H | 132–134 |
| MC 512 | O | H | H | 3,5-Me$_2$-c-hex | H | H | H | H | H | 178–181 |
| MC 531 | O | Me | H | 2,5-Me$_2$-c-hex | H | H | H | H | H | 196–198 |
| MC 1114 | O | H | H | Sec-but | F | H | H | H | F | 87–88 |
| MC 1103 | O | H | H | c-pent | F | H | H | H | F | 183.5–184.5 |
| MC 843 | S | H | H | benzyloxymeth | H | H | H | H | H | 181–183 |
| MC 796 | S | H | Ph | Sec-but | H | H | H | H | H | 157–158 |
| MC 890 | S | H | Me | iso-prop | H | H | H | H | H | 118–119 |
| MC 892 | S | H | Me | c-pent | H | H | H | H | H | 95–96 |
| MC 898 | S | H | Me | c-hex | H | H | H | H | H | 142–143 |
| MC 899 | S | H | Et | iso-prop | H | H | H | H | H | 144–145 |
| MC 900 | S | H | Et | c-pent | H | H | H | H | H | 168–169 |
| MC 903 | S | H | Et | c-hex | H | H | H | H | H | 175.5–176.5 |
| MC 806 | S | H | H | Sec-but | Me | H | H | H | H | 118–119 |
| MC 842 | S | H | H | c-pent | Me | H | H | H | H | 142–144 |
| MC 809 | S | H | H | Sec-but | H | H | Me | H | H | 107.5–108.5 |
| MC 817 | S | H | H | Sec-but | NO$_2$ | H | H | H | H | 148.0–148.5 |
| MC 897 | S | H | H | Sec-but | H | NO$_2$ | H | H | H | 127–128 |
| MC 863 | S | H | H | Sec-but | H | H | NO$_2$ | H | H | 128–130 |
| MC 854 | S | H | H | Sec-but | Cl | H | H | H | H | 120–121 |
| MC 857 | S | H | H | Sec-but | H | Cl | H | H | H | 98–99 |
| MC 859 | S | H | H | Sec-but | H | H | Cl | H | H | 125–126 |
| MC 880 | S | H | H | Sec-but | F | H | H | H | H | 106–107 |
| MC 884 | S | H | H | Sec-but | H | F | H | H | H | 96–97 |
| MC 889 | S | H | H | Sec-but | H | H | F | H | H | 98–99 |
| MC 825 | S | H | H | Sec-but | NH$_2$ | H | H | H | H | 143–144 |
| MC 960 | S | H | H | Sec-but | H | H | NH$_2$ | H | H | 128–130 |
| MC 868 | S | H | H | Sec-but | CF$_3$ | H | H | H | H | 125–126 |
| MC 959 | S | H | H | Sec-but | H | H | CF$_3$ | H | H | 144–145 |
| MC 952 | S | H | H | Sec-but | OMe | H | H | H | H | 123–124 |
| MC 957 | S | H | H | Sec-but | H | OMe | H | H | H | 78–80 |
| MC 964 | S | H | H | Sec-but | H | H | OMe | H | H | 112–113 |
| MC 1041 | S | H | H | Sec-but | H | F | H | H | H | 122–123 |
| MC 1042 | S | H | H | Sec-but | H | Me | H | H | H | 119–120 |
| MC877 | S | H | H | Me | Cl | H | H | H | Cl | 237–238 |
| MC878 | S | H | H | iso-prop | Cl | H | H | H | Cl | 230–231 |
| MC886 | S | H | H | n-but | Cl | H | H | H | Cl | 153–154 |
| MC885 | S | H | H | iso-but | Cl | H | H | H | Cl | 143.5–144.5 |
| MC815 | S | H | H | sec-but | Cl | H | H | H | Cl | 183–184 |
| MC888 | S | H | H | c-pent | Cl | H | H | H | Cl | 185–186 |
| MC891 | S | H | H | c-hex | Cl | H | H | H | Cl | 200–201 |
| MC871 | S | H | H | Me | F | H | H | H | F | 197–198 |
| MC860 | S | H | H | iso-prop | F | H | H | H | F | 174–175 |
| MC872 | S | H | H | n-but | F | H | H | H | F | 126–127 |
| MC866 | S | H | H | iso-but | F | H | H | H | F | 136–137 |
| MC848 | S | H | H | sec-but | F | H | H | H | F | 149–150 |
| MC867 | S | H | H | c-pent | F | H | H | H | F | 168–169 |
| MC870 | S | H | H | c-hex | F | H | H | H | F | 164–165 |
| MC1001 | S | H | Me | iso-prop | Cl | H | H | H | Cl | 196–196.5 |
| MC996 | S | H | Me | c-pent | Cl | H | H | H | Cl | 181–182 |
| MC1016 | S | H | Me | c-hex | Cl | H | H | H | Cl | 211–212 |
| MC1000 | S | H | Et | iso-prop | Cl | H | H | H | Cl | 166–168 |
| MC1002 | S | H | Et | c-pent | Cl | H | H | H | Cl | 168–169 |
| MC1003 | S | H | Et | c-hex | Cl | H | H | H | Cl | 198–199 |
| MC1007 | S | H | Me | iso-prop | F | H | H | H | F | 155–156 |
| MC1044 | S | H | Me | iso-but | F | H | H | H | F | 159–160 |
| MC1045 | S | H | Me | n-but | F | H | H | H | F | 149–150 |

TABLE 1-continued

Physical and Chemical Data of MC Compounds

| | | | | | | | | | | | |
|---|---|---|---|---|---|---|---|---|---|---|---|
| MC1110 | S | H | Me | sec-but | F | | H | H | H | F | 133–134 |
| MC1008 | S | H | Me | c-pent | F | | H | H | H | F | 165.5–166.5 |
| MC1013 | S | H | Me | c-hex | F | | H | H | H | F | 206–207 |
| MC1005 | S | H | Et | iso-prop | F | | H | H | H | F | 149–150 |
| MC1006 | S | H | Et | c-pent | F | | H | H | H | F | 141–143 |
| MC1014 | S | H | Et | c-hex | F | | H | H | H | F | 154–155 |
| MC971 | S | H | Me | iso-prop | | CH=CH—CH=CH | H | H | H | | 161–162 |
| MC972 | S | H | Me | c-pent | | CH=CH—CH=CH | H | H | H | | 140–141 |
| MC974 | S | H | Me | c-hex | | CH=CH—CH=CH | H | H | H | | 177–178 |
| MC969 | S | H | Et | iso-prop | | CH=CH—CH=CH | H | H | H | | 163–164 |
| MC973 | S | H | Et | c-pent | | CH=CH—CH=CH | H | H | H | | oil |
| MC975 | S | H | Et | c-hex | | CH=CH—CH=CH | H | H | H | | 126–127 |
| MC844 | S | Me | H | sec-but | Me | | H | H | H | H | 177–178 |
| MC845 | S | Me | H | sec-but | H | | H | Me | H | H | 127–128 |
| MC925 | S | Me | H | sec-but | H | | $NO_2$ | H | H | H | 163–164 |
| MC924 | S | Me | H | sec-but | H | | H | $NO_2$ | H | H | 178–180 |
| MC909 | S | Me | H | sec-but | Cl | | H | H | H | H | 170–171 |
| MC910 | S | Me | H | sec-but | H | | Cl | H | H | H | 145–146 |
| MC911 | S | Me | H | sec-but | H | | H | Cl | H | H | 163–165 |
| MC913 | S | Me | H | sec-but | F | | H | H | H | H | 120.5–121.5 |
| MC918 | S | Me | H | sec-but | H | | F | F | H | H | 146–147 |
| MC919 | S | Me | H | sec-but | H | | H | F | H | H | 154–155 |
| MC912 | S | Me | H | Me | Cl | | H | H | H | Cl | 206–261 |
| MC914 | S | Me | H | iso-prop | Cl | | H | H | H | Cl | 241–242 |
| MC920 | S | Me | H | n-but | Cl | | H | H | H | Cl | 179–180 |
| MC916 | S | Me | H | iso-but | Cl | | H | H | H | Cl | 208–209 |
| MC850 | S | Me | H | sec-but | Cl | | H | H | H | Cl | 204–205 |
| MC915 | S | Me | H | c-pent | Cl | | H | H | H | Cl | 252–253 |
| MC917 | S | Me | H | c-hex | Cl | | H | H | H | Cl | 237–238 |
| MC869 | S | Me | H | Me | F | | H | H | H | F | 218.5–219.5 |
| MC881 | S | Me | H | iso-prop | F | | H | H | H | F | 164–165 |
| MC905 | S | Me | H | n-but | F | | H | H | H | F | 178–179 |
| MC921 | S | Me | H | iso-but | F | | H | H | H | F | 161–162 |
| MC849 | S | Me | H | sec-but | F | | H | H | H | F | 128–129 |
| MC922 | S | Me | H | c-pent | F | | H | H | H | F | 192–193 |
| MC923 | S | Me | H | c-hex | F | | H | H | H | F | 191–192 |
| MC1060 | S | Me | Me | Me | F | | H | H | H | F | 202–203 |
| MC1109 | S | Me | Me | sec-but | F | | H | H | H | F | 135–136 |
| MC1047 | S | Me | Me | c-pent | F | | H | H | H | F | 196–197 |
| MC798 | S | Et | H | sec-but | H | | H | H | H | H | 140–141 |
| MC1037 | S | Et | H | iso-prop | F | | H | H | H | F | 174–175 |
| MC1038 | S | Et | H | sec-but | F | | H | H | H | F | 150–151 |
| MC804 | S | Et | H | sec-but | | CH=CH—CH=CH | H | H | H | | 198.5–199.5 |
| MC1039 | S | i-pro | H | iso-prop | F | | H | H | H | F | 167–168 |
| MC852 | S | allyl | H | sec-but | H | | H | H | H | H | 127.5–128.5 |
| MC856 | S | n-pro | H | sec-but | H | | H | H | H | H | 108–109 |
| MC834 | S | n-but | H | sec-but | H | | H | H | H | H | oil |
| MC1119 | NH | H | H | ethyl | F | | H | H | H | F | 138–140 |
| MC1078 | NH | H | H | n-prop | F | | H | H | H | F | 136–137 |
| MC979 | NH | H | H | iso-prop | F | | H | H | H | F | 150–151 |
| MC980 | NH | H | H | c-prop | F | | H | H | H | F | 183–184 |
| MC1077 | NH | H | H | n-but | F | | H | H | H | F | 130–131 |
| MC945 | NH | H | H | sec-but | F | | H | H | H | F | 140–141 |
| MC1043 | NH | H | H | MeOethyl | F | | H | H | H | F | 120–121 |
| MC1022 | NH | H | H | c-pent | F | | H | H | H | F | oil |
| MC1049 | NH | H | H | c-hex | F | | H | H | H | F | 143–144 |
| MC1048 | NH | H | Me | c-pent | F | | H | H | H | F | oil |
| MC1118 | NH | Me | H | iso-prop | F | | H | H | H | F | 165–166 |
| MC1130 | NH | Me | H | sec-but | F | | H | H | H | F | oil |
| MC1050 | NH | Me | H | c-pent | F | | H | H | H | F | 115–117 |
| MC1105 | NH | Me | H | benzyl | F | | H | H | H | F | 182–183 |
| MC1129 | NH | Me | Me | c-pent | F | | H | H | H | F | oil |
| MC1167 | NH | H | H | Me | F | | H | H | H | F | 202–203 |
| MC1168 | NH | Me | H | Me | F | | H | H | H | F | 210–211 |
| MC1186 | NH | Me | H | n-prop | F | | H | H | H | F | 156–157 |
| MC1185 | NH | Me | H | n-but | F | | H | H | H | F | 192–193 |
| MC1178 | NH | H | Me | Me | F | | H | H | H | F | 145–146 |
| MC1190 | NH | H | Me | n-prop | F | | H | H | H | F | oil |
| MC1191 | NH | H | Me | iso-prop | F | | H | H | H | F | oil |
| MC1189 | NH | H | Me | n-but | F | | H | H | H | F | oil |
| MC1192 | NH | H | Me | sec-but | F | | H | H | H | F | oil |
| MC1180 | NH | H | Me | c-hex | F | | H | H | H | F | oil |
| MC1170 | NH | Me | Me | Me | F | | H | H | H | F | 193–194 |
| MC1187 | NH | Me | Me | n-but | F | | H | H | H | F | oil |
| MC1181 | NH | Me | Me | c-hex | F | | H | H | H | F | oil |
| MC1182 | N | H | H | $Me_2$ | F | | H | H | H | F | 210–211 |
| MC1183 | N | H | H | Me-piperaz | F | | H | H | H | F | 195–196 |

TABLE 1-continued

Physical and Chemical Data of MC Compounds

| Compd. | | | | | | | | | | |
|---|---|---|---|---|---|---|---|---|---|---|
| MC1188 | N | H | H | morph | F | H | H | H | F | 215–216 |
| MC1193 | N | H | H | thiomorph | F | H | H | H | F | 233–234 |
| MC1194 | N | H | H | piperid | F | H | H | H | F | 209–210 |
| MC1196 | N | H | H | pyrrolid | F | H | H | H | F | 233–234 |
| MC1202 | N | H | H | $Et_2$ | F | H | H | H | F | 159–160 |
| MC1204 | N | H | H | (n-prop)$_2$ | F | H | H | H | F | 111–112 |
| MC1195 | N | Me | H | $Me_2$ | F | H | H | H | F | 237–238 |
| MC1203 | N | Me | H | Me-piperaz | F | H | H | H | F | 235–236 |
| MC1205 | N | Me | H | morph | F | H | H | H | F | 244–245 |
| MC1206 | N | Me | H | thiomorph | F | H | H | H | F | 255–256 |
| MC1137 | S | Me | Me | iso-prop | F | H | H | H | F | 177–178 |
| MC1175 | S | Me | Me | n-but | F | H | H | H | F | 122–123 |
| MC1153 | S | Me | Me | iso-but | F | H | H | H | F | 152–153 |
| MC1174 | S | Me | Me | c-hex | F | H | H | H | F | 208–209 |
| MC1161 | S | H | H | MeSMe | F | H | H | H | F | 159–160 |
| MC1162 | S | Me | H | MeSMe | F | H | H | H | F | 183–184 |
| MC1157 | S | Et | H | MeSMe | F | H | H | H | F | 153–154 |
| MC1145 | S | i-pro | H | MeSMe | F | H | H | H | F | 158.5–160 |
| MC1140 | S | H | H | MeSMe | H | H | H | H | H | 117.5–118 |

| Compd. | Recryst. Solvent | % yield | Formula [a] |
|---|---|---|---|
| MC 507 | Petrol. Ether/diethyl ether | 22 | $C_{19}H_{24}N_2O_2$ |
| MC 508 | Petrol. Ether/diethyl ether | 28 | $C_{19}H_{24}N_2O_2$ |
| MC 512 | Petrol. Ether/diethyl ether | 12 | $C_{19}H_{24}N_2O_2$ |
| MC 531 | Petrol. Ether/diethyl ether | 18 | $C_{20}H_{26}N_2O_2$ |
| MC 1114 | Petrol. Ether/diethyl ether | 28 | $C_{15}H_{16}F_2N_2O_2$ |
| MC 1103 | Benzene | 52 | $C_{16}H_{16}F_2N_2O_2$ |
| MC 843 | Cyclohexane/benzene | 38 | $C_{19}H_{18}N_2O_2S$ |
| MC 796 | n-hexane/cyclohexane | 78 | $C_{21}H_{22}N_2OS$ |
| MC 890 | n-hexane | 88 | $C_{15}H_{18}N_2OS$ |
| MC 892 | n-hexane | 65 | $C_{17}H_{20}N_2OS$ |
| MC 898 | n-hexane | 59 | $C_{16}H_{22}N_2OS$ |
| MC 899 | Cyclohexane | 85 | $C_{16}H_{20}N_2OS$ |
| MC 900 | Cyclohexane | 69 | $C_{18}H_{22}N_2OS$ |
| MC 903 | Cyclohexane | 60 | $C_{19}H_{24}N_2OS$ |
| MC 806 | n-hexane/cyclohexane | 67 | $C_{16}H_{20}N_2OS$ |
| MC 842 | Cyclohexane | 61 | $C_{17}H_{20}N_2OS$ |
| MC 809 | n-hexane | 56 | $C_{16}H_{20}N_2OS$ |
| MC 817 | Cyclohexane/benzene | 68 | $C_{15}H_{17}N_3O_3S$ |
| MC 897 | Cyclohexane/benzene | 54 | $C_{15}H_{17}N_3O_3S$ |
| MC 863 | Petrol. Ether/diethyl ether | 100 | $C_{15}H_{17}N_3O_3S$ |
| MC 854 | n-hexane/cyclohexane | 58 | $C_{15}H_{17}N_3O_3S$ |
| MC 857 | Cyclohexane | 92 | $C_{15}H_{17}N_3O_3S$ |
| MC 859 | Cyclohexane | 74 | $C_{15}H_{17}ClN_2OS$ |
| MC 880 | n-hexane/cyclohexane | 68 | $C_{15}H_{17}ClN_2OS$ |
| MC 884 | Cyclohexane | 67 | $C_{15}H_{17}FN_2OS$ |
| MC 889 | n-hexane | 94 | $C_{15}H_{17}FN_2OS$ |
| MC 825 | Cyclohexane/benzene | 74 | $C_{15}H_{19}N_2OS$ |
| MC 960 | Cyclohexane | 77 | $C_{15}H_{19}N_2OS$ |
| MC 868 | Cyclohexane | 89 | $C_{16}H_{17}F_3N_2OS$ |
| MC 959 | Cyclohexane | 75 | $C_{16}H_{17}F_3N_2OS$ |
| MC 952 | Cyclohexane | 69 | $C_{16}H_{20}N_2O_2S$ |
| MC 957 | n-hexane/Cyclohexane | 71 | $C_{16}H_{20}N_2O_2S$ |
| MC 964 | Cyclohexane | 63 | $C_{16}H_{20}N_2O_2S$ |
| MC 1041 | Cyclohexane | 68 | $C_{15}H_{20}F_2N_2OS$ |
| MC 1042 | n-hexane | 72 | $C_{17}H_{22}N_2OS$ |
| MC877 | benzene | 98 | $C_{12}H_{20}Cl_2N_2OS$ |
| MC878 | benzene | 81 | $C_{14}H_{14}Cl_2N_2OS$ |
| MC886 | cyclohexane | 62 | $C_{15}H_{16}Cl_2N_2OS$ |
| MC885 | cyclohexane | 56 | $C_{15}H_{16}Cl_2N_2OS$ |
| MC815 | cyclohexane/benzene | 55 | $C_{15}H_{16}Cl_2N_2OS$ |
| MC888 | cyclohexane | 54 | $C_{16}H_{16}Cl_2N_2OS$ |
| MC891 | cyclohexane/benzene | 49 | $C_{17}H_{18}Cl_2N_2OS$ |
| MC871 | benzene | 95 | $C_{12}H_{19}F_2N_2OS$ |
| MC860 | cyclohexane | 74 | $C_{14}H_{14}F_2N_2OS$ |
| MC872 | cyclohexane | 46 | $C_{15}H_{16}F_2N_2OS$ |
| MC866 | cyclohexane | 49 | $C_{15}H_{16}F_2N_2OS$ |
| MC848 | n-hexane/cyclohexane | 48 | $C_{15}H_{16}F_2N_2OS$ |
| MC867 | cyclohexane | 45 | $C_{16}H_{16}FN_2OS$ |
| MC870 | cyclohexane | 40 | $C_{17}H_{18}F_2N_2OS$ |
| MC1001 | cyclohexane/benzene | 52 | $C_{13}H_{16}Cl_2N_2OS$ |
| MC996 | cyclohexane | 45 | $C_{17}H_{18}Cl_2N_2OS$ |
| MC1016 | cyclohexane/benzene | 42 | $C_{16}H_{20}Cl_2N_2OS$ |
| MC1000 | diethyl ether | 54 | $C_{16}H_{18}Cl_2N_2OS$ |
| MC1002 | diethyl ether | 40 | $C_{18}H_{20}Cl_2N_2OS$ |
| MC1003 | cyclohexane | 41 | $C_{19}H_{22}Cl_2N_2OS$ |

TABLE 1-continued

Physical and Chemical Data of MC Compounds

| | | | |
|---|---|---|---|
| MC1007 | cyclohexane | 53 | $C_{15}H_{16}F_2N_2OS$ |
| MC1044 | cyclohexane | 49 | $C_{16}H_{18}F_2N_2OS$ |
| MC1045 | cyclohexane | 58 | $C_{16}H_{18}F_2N_2OS$ |
| MC1110 | n-hexane | 75 | $C_{16}H_{18}F_2N_2OS$ |
| MC1008 | cyclohexane | 60 | $C_{17}H_{18}F_2N_2OS$ |
| MC1013 | benzene | 44 | $C_{18}H_{20}F_2N_2OS$ |
| MC1005 | cyclohexane | 40 | $C_{16}H_{18}F_2N_2OS$ |
| MC1006 | cyclohexane | 45 | $C_{18}H_{20}F_2N_2OS$ |
| MC1014 | cyclohexane | 51 | $C_{19}H_{22}F_2N_2OS$ |
| MC971 | n-hexane/cyclohexane | 58 | $C_{19}H_{20}N_2OS$ |
| MC972 | n-hexane/cyclohexane | 49 | $C_{21}H_{22}N_2OS$ |
| MC974 | n-hexane | 45 | $C_{22}H_{24}N_2OS$ |
| MC969 | cyclohexane | 54 | $C_{20}H_{22}N_2OS$ |
| MC973 | — | 48 | $C_{22}H_{24}N_2OS$ |
| MC975 | n-hexane | 41 | $C_{23}H_{26}N_2OS$ |
| MC844 | cyclohexane | 55 | $C_{17}H_{22}N_2OS$ |
| MC845 | n-hexane | 61 | $C_{17}H_{22}N_2OS$ |
| MC925 | cyclohexane/benzene | 88 | $C_{16}H_{19}N_3OS$ |
| MC924 | cyclohexane/benzene | 100 | $C_{16}H_{19}N_3O_3S$ |
| MC909 | cyclohexane | 68 | $C_{16}H_{19}ClN_2OS$ |
| MC910 | cyclohexane | 75 | $C_{16}H_{19}ClN_2OS$ |
| MC911 | cyclohexane | 79 | $C_{16}H_{19}ClN_2OS$ |
| MC913 | cyclohexane | 65 | $C_{16}H_{19}FN_2OS$ |
| MC918 | cyclohexane | 72 | $C_{16}H_{19}FN_2OS$ |
| MC919 | cyclohexane | 69 | $C_{16}H_{19}FN_2OS$ |
| MC912 | benzene | 93 | $C_{18}H_{12}Cl_2N_2OS$ |
| MC914 | cyclohexane/benzene | 78 | $C_{15}H_{16}Cl_2N_2OS$ |
| MC920 | cyclohexane | 52 | $C_{16}H_{18}Cl_2N_2OS$ |
| MC916 | cyclohexane | 63 | $C_{16}H_{18}Cl_2N_2OS$ |
| MC850 | cyclohexane | 53 | $C_{16}H_{18}Cl_2N_2OS$ |
| MC915 | cyclohexane/benzene | 49 | $C_{17}H_{18}Cl_2N_2OS$ |
| MC917 | cyclohexane | 48 | $C_{18}H_{20}Cl_2N_2OS$ |
| MC869 | benzene | 92 | $C_{19}H_{12}F_2N_2OS$ |
| MC881 | cyclohexane | 76 | $C_{13}H_{16}F_2N_2OS$ |
| MC905 | cyclohexane | 65 | $C_{16}H_{18}F_2N_2OS$ |
| MC921 | cyclohexane | 59 | $C_{16}H_{18}F_2N_2OS$ |
| MC849 | n-hexane | 49 | $C_{16}H_{18}F_2N_2OS$ |
| MC922 | cyclohexane | 54 | $C_{17}H_{18}F_2N_2OS$ |
| MC923 | cyclohexane | 49 | $C_{18}H_{20}F_2N_2OS$ |
| MC1060 | cyclohexane/benzene | 49 | $C_{18}H_{14}F_2N_2OS$ |
| MC1109 | cyclohexane | 55 | $C_{17}H_{20}F_2N_2OS$ |
| MC1047 | cyclohexane | 60 | $C_{18}H_{20}F_2N_2OS$ |
| MC798 | n-hexane | 47 | $C_{17}H_{22}N_2OS$ |
| MC1037 | benzene | 78 | $C_{16}H_{18}F_2N_2OS$ |
| MC1038 | n-hexane/cyclohexane | 62 | $C_{17}H_{20}F_2N_2OS$ |
| MC804 | cyclohexane | 42 | $C_{21}H_{24}N_2OS$ |
| MC1039 | n-hexane | 76 | $C_{17}H_{20}F_2N_2OS$ |
| MC852 | cyclohexane | 68 | $C_{16}H_{22}N_2OS$ |
| MC856 | n-hexane | 42 | $C_{21}H_{24}N_2OS$ |
| MC834 | — | 32 | $C_{19}H_{26}N_2OS$ |
| MC1119 | n-hexane/cyclohexane | 50 | $C_{14}H_{14}F_2N_3O$ |
| MC1078 | cyclohexane | 49 | $C_{14}H_{15}F_2N_3O$ |
| MC979 | diethyl ether | 58 | $C_{14}H_{15}F_2N_3O$ |
| MC980 | cyclohexane/benzene | 68 | $C_{14}H_{16}F_2N_3O$ |
| MC1077 | n-hexane | 60 | $C_{15}H_{17}F_2N_3O$ |
| MC945 | diethyl ether | 80 | $C_{15}H_{17}F_2N_3O$ |
| MC1043 | acetonitrile | 78 | $C_{14}H_{15}F_2N_3O_2$ |
| MC1022 | — | 74 | $C_{16}H_{13}F_2N_3O$ |
| MC1049 | diethyl ether | 45 | $C_{17}H_{14}F_2N_3O$ |
| MC1048 | — | 48 | $C_{17}H_{14}F2N_3O$ |
| MC1118 | n-hexane | 53 | $C_{13}H_{17}F_2N_3O$ |
| MC1130 | — | 56 | $C_{16}H_{14}F_2N_3O$ |
| MC1050 | n-hexane/cyclohexane | 60 | $C_{17}H_{14}F_2N_3O$ |
| MC1105 | cyclohexane/benzene | 82 | $C_{14}H_{17}F_2N_3O$ |
| MC1129 | — | 38 | $C_{14}H_{21}F_2N_3O$ |
| MC1167 | acetonitrile | 39 | $C_{12}H_{11}F_2N_3O$ |
| MC1168 | acetonitrile | 48 | $C_{13}H_{13}F_2N_3O$ |
| MC1186 | acetonitrile | 62 | $C_{13}H_{12}F_2N_3O$ |
| MC1185 | acetonitrile | 68 | $C_{16}H_{14}F_2N_3O$ |
| MC1178 | acetonitrile | 34 | $C_{13}H_{13}F_2N_3O$ |
| MC1190 | — | 45 | $C_{13}H_{17}F_2N_3O$ |
| MC1191 | — | 54 | $C_{15}H_{17}F_2N_3O$ |
| MC1189 | — | 55 | $C_{16}H_{19}F_2N_3O$ |
| MC1192 | — | 59 | $C_{16}H_{19}F_2N_3O$ |
| MC1180 | — | 62 | $C_{18}H_{21}F_2N_3O$ |
| MC1170 | cyclohexane/benzene | 34 | $C_{14}H_{15}F_2N_3O$ |
| MC1187 | — | 49 | $C_{17}H_{21}F_2N_3O$ |

TABLE 1-continued

Physical and Chemical Data of MC Compounds

| | | | |
|---|---|---|---|
| MC1181 | — | 54 | $C_{10}H_{23}F_2N_3O$ |
| MC1182 | cyclohexane/benzene | 88 | $C_{13}H_{13}F_2N_3O$ |
| MC1183 | acetonitrile | 84 | $C_{16}H_{18}F_2N_3O$ |
| MC1188 | acetonitrile | 75 | $C_{15}H_{13}F_2N_3O_2$ |
| MC1193 | acetonitrile | 78 | $C_{15}H_{13}F_2N_3OS$ |
| MC1194 | acetonitrile | 68 | $C_{16}H_{17}F_2N_3O$ |
| MC1196 | acetonitrile | 52 | $C_{15}H_{15}F_2N_3O$ |
| MC1202 | acetonitrile | 43 | $C_{15}H17F_2N_3O$ |
| MC1204 | n-hexane | 32 | $C_{17}H_{21}F_2N_3O$ |
| MC1195 | acetonitrile | 80 | $C_{14}H_{13}F_2N_3O$ |
| MC1203 | acetonitrile | 62 | $C_{17}H_{20}F_2N_3O$ |
| MC1205 | acetonitrile | 65 | $C_{16}H_{17}F_2N_3O_2$ |
| MC1206 | acetonitrile | 54 | $C_{16}H_{17}F_2N_2OS$ |
| MC1137 | n-hexane/cyclohexane | 45 | $C_{16}H_{18}F_2N_2OS$ |
| MC1175 | n-hexane | 51 | $C_{17}H_{20}F_2N_2OS$ |
| MC1153 | cyclohexane | 58 | $C_{17}H_{20}F_2N_2OS$ |
| MC1174 | n-hexane/cyclohexane | 48 | $C_{19}H_{22}F_2N_2OS$ |
| MC1161 | cyclohexane/benzene | 72 | $C_{13}H_{12}F_2N_2OS_2$ |
| MC1162 | cyclohexane/benzene | 70 | $C_{14}H_{14}F_2N_2OS_2$ |
| MC1157 | cyclohexane | 69 | $C_{15}H_{16}F_2N_2OS_2$ |
| MC1145 | cyclohexane | 62 | $C_{16}H_{18}F_2N_2OS_2$ |
| MC1140 | n-hexane | 64 | $C_{13}H_{14}N_2OS_2$ |

[a] All compounds were analyzed for C, H, N, S, and, when required, Cl and F; analytical results were within ±0.4% of theroretical values.

TABLE 2

Cytotoxicity and anti-HIV-1 Activity of MC Compounds.

(A)

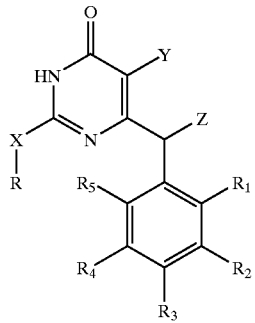

| | | | | | | | | | | [μM] | | |
|---|---|---|---|---|---|---|---|---|---|---|---|---|
| Compd. | X | Y | Z | R | $R^1$ | $R^2$ | $R^3$ | $R^4$ | $R^5$ | $CC_{50}$[b] | $EC_{50}$[c] | SI[d] |
| MC 507 | O | H | H | 2,5-Me$_2$-c-hex | H | H | H | H | H | 143 | 3.5 | 40 |
| MC 508 | O | H | H | 4,5-Me$_2$-c-hex | H | H | H | H | H | 58 | 6.4 | 9 |
| MC 512 | O | H | H | 3,5-Me$_2$-c-hex | H | H | H | H | H | >200 | 30 | >6.7 |
| MC 531 | O | Me | H | 2,5-Me$_2$-c-hex | H | H | H | H | H | 138 | 3.5 | 39 |
| MC 1114 | O | H | H | sec-but | F | H | H | H | F | 130 | 25 | 52 |
| MC 1103 | O | H | H | c-pent | F | H | H | H | F | >200 | 20 | >10 |
| MC 843 | S | H | H | benzoyloxy-methyl | H | H | H | H | H | >200 | 45 | >4 |
| MC 796 | S | H | Ph | sec-but | H | H | H | H | H | 61 | >61 | — |
| MC 890 | S | H | Me | iso-prop | H | H | H | H | H | >200 | .9 | >222 |
| MC 892 | S | H | Me | c-pent | H | H | H | H | H | 159 | .6 | 333 |
| MC 898 | S | H | Me | c-hex | H | H | H | H | H | 149 | .6 | 248 |
| MC 899 | S | H | Et | iso-prop | H | H | H | H | H | 200 | .8 | 250 |
| MC 900 | S | H | Et | c-pent | H | H | H | H | H | >200 | 1.0 | >200 |
| MC 903 | S | H | Et | c-hex | H | H | H | H | H | >200 | 1.3 | >154 |
| MC 806 | S | H | H | sec-but | Me | H | H | H | H | >200 | 1.8 | >111 |
| MC 842 | S | H | H | c-pent | Me | H | H | H | H | >200 | 3.4 | >59 |
| MC 809 | S | H | H | sec-but | H | H | Me | H | H | 200 | 0.6 | 333.3 |
| MC 817 | S | H | H | sec-but | NO$_2$ | H | H | H | H | >200 | 0.25 | >800 |
| MC 897 | S | H | H | sec-but | H | NO$_2$ | H | H | H | 157 | 0.40 | 392 |
| MC 863 | S | H | H | sec-but | H | H | NO$_2$ | H | H | 151 | 1.5 | 101 |
| MC 854 | S | H | H | sec-but | Cl | H | H | H | H | 200 | 1 | 200 |
| MC 857 | S | H | H | sec-but | H | Cl | H | H | H | 116 | 2 | 58 |
| MC 859 | S | H | H | sec-but | H | H | Cl | H | H | 120 | 5 | 24 |
| MC 880 | S | H | H | sec-but | F | H | H | H | H | 200 | 0.26 | 769 |

TABLE 2-continued

Cytotoxicity and anti-HIV-1 Activity of MC Compounds.

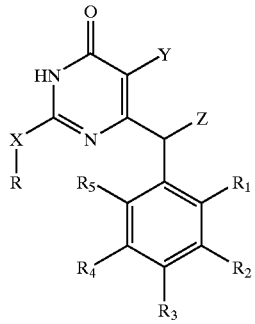

(A)

| Compd. | X | Y | Z | R | R¹ | R² | R³ | R⁴ | R⁵ | $CC_{50}$[b] [μM] | $EC_{50}$[c] [μM] | SI[d] |
|---|---|---|---|---|---|---|---|---|---|---|---|---|
| MC 884 | S | H | H | sec-but | H | F | H | H | H | >200 | 0.7 | >286 |
| MC 889 | S | H | H | sec-but | H | H | F | H | H | >200 | 8.7 | 23 |
| MC 825 | S | H | H | sec-but | $NH_2$ | H | H | H | H | >200 | 21.2 | >9 |
| MC 960 | S | H | H | sec-but | H | H | $NH_2$ | H | H | >200 | 23 | >8 |
| MC 868 | S | H | H | sec-but | $CF_3$ | H | H | H | H | >200 | 32 | 6.2 |
| MC 959 | S | H | H | sec-but | H | H | $CF_3$ | H | H | 200 | 25 | 8 |
| MC 952 | S | H | H | sec-but | OMe | H | H | H | H | >200 | 1.96 | >208 |
| MC 957 | S | H | H | sec-but | H | OMe | H | H | H | >200 | 1.2 | >166 |
| MC 964 | S | H | H | sec-but | H | H | OMe | H | H | 147 | 14 | 10.5 |
| MC 1041 | S | H | H | sec-but | H | F | H | H | H | >200 | 1.4 | >143 |
| MC 1042 | S | H | H | sec-but | H | Me | H | H | H | 133 | 0.6 | 222 |
| MC 877 | S | H | H | Me | Cl | H | H | H | Cl | >200 | 3.2 | >62 |
| MC 878 | S | H | H | iso-prop | Cl | H | H | H | Cl | >200 | 1.9 | >105 |
| MC 886 | S | H | H | n-but | Cl | H | H | H | Cl | >200 | 0.44 | >454 |
| MC 885 | S | H | H | iso-but | Cl | H | H | H | Cl | >200 | 0.45 | >444 |
| MC 815 | S | H | H | sec-but | Cl | H | H | H | Cl | >200 | 0.14 | >1,428 |
| MC 888 | S | H | H | c-pent | Cl | H | H | H | Cl | >200 | 0.4 | >500 |
| MC 891 | S | H | H | c-hex | Cl | H | H | H | Cl | >200 | 0.6 | >333 |
| MC 871 | S | H | H | Me | F | H | H | H | F | 200 | 0.81 | 247 |
| MC 860 | S | H | H | iso-prop | F | H | H | H | F | >200 | 0.2 | >1,000 |
| MC 872 | S | H | H | n-but | F | H | H | H | F | 162 | 0.18 | 900 |
| MC 866 | S | H | H | iso-but | F | H | H | H | F | 182 | 0.14 | 1,300 |
| MC 848 | S | H | H | sec-but | F | H | H | H | F | 200 | 0.04 | 5,000 |
| MC 867 | S | H | H | c-pent | F | H | H | H | F | >200 | 0.08 | >2,500 |
| MC 870 | S | H | H | c-hex | F | H | H | H | F | 200 | 0.08 | 2,500 |
| MC 1001 | S | H | Me | iso-prop | Cl | H | H | H | Cl | 117 | 1.2 | 97.5 |
| MC 996 | S | H | Me | c-pent | Cl | H | H | H | Cl | 78.3 | 1.0 | 78.3 |
| MC 1016 | S | H | Me | c-hex | Cl | H | H | H | Cl | >200 | 2.9 | >69 |
| MC 1000 | S | H | Et | iso-prop | Cl | H | H | H | Cl | >200 | 0.4 | >500 |
| MC 1002 | S | H | Et | c-pent | Cl | H | H | H | Cl | 23.4 | 1.0 | 23.4 |
| MC 1003 | S | H | Et | c-hex | Cl | H | H | H | Cl | >200 | 3.6 | >55.5 |
| MC 1007 | S | H | Me | iso-prop | F | H | H | H | F | 167 | 0.05 | 3,340 |
| MC 1044 | S | H | Me | iso-but | F | H | H | H | F | >200 | 0.05 | >4,000 |
| MC 1045 | S | H | Me | n-but | F | H | H | H | F | >200 | 0.07 | 2,857 |
| MC 1110 | S | H | Me | sec-but | F | H | H | H | F | >200 | 0.03 | >6,666 |
| MC 1008 | S | H | Me | c-pent | F | H | H | H | F | >200 | 0.03 | >6,666 |
| MC 1013 | S | H | Me | c-hex | F | H | H | H | F | >200 | 0.16 | >1,250 |
| MC 1005 | S | H | Et | iso-prop | F | H | H | H | F | 70 | 0.08 | 875 |
| MC 1006 | S | H | Et | c-pent | F | H | H | H | F | 200 | 0.15 | 1,333 |
| MC 1014 | S | H | Et | c-hex | F | H | H | H | F | 130 | 0.05 | 2,600 |
| MC 971 | S | H | Me | iso-prop | CH=CH—CH=CH | | H | H | H | 119 | 1.1 | 108 |
| MC 972 | S | H | Me | c-pent | CH=CH—CH=CH | | H | H | H | 93 | 0.5 | 186 |
| MC 974 | S | H | Me | c-hex | CH=CH—CH=CH | | H | H | H | 45 | 0.14 | 321.4 |
| MC 969 | S | H | Et | iso-prop | CH=CH—CH=CH | | H | H | H | 50 | 1.5 | 33.3 |
| MC 973 | S | H | Et | c-pent | CH=CH—CH=CH | | H | H | H | 51 | 3.0 | 17 |
| MC 975 | S | H | Et | c-hex | CH=CH—CH=CH | | H | H | H | 16.9 | 0.18 | 94 |
| MC 844 | S | Me | H | sec-but | Me | H | H | H | H | >200 | 1.7 | >118 |
| MC 845 | S | Me | H | sec-but | H | H | Me | H | H | 26 | 0.8 | 32 |
| MC 925 | S | Me | H | sec-but | H | $NO_2$ | H | H | H | >200 | 0.35 | >571 |
| MC 924 | S | Me | H | sec-but | H | H | $NO_2$ | H | H | >200 | 2 | >100 |
| MC 909 | S | Me | H | sec-but | Cl | H | H | H | H | >200 | 0.27 | >741 |
| MC 910 | S | Me | H | sec-but | H | Cl | H | H | H | >200 | 0.96 | >208 |
| MC 911 | S | Me | H | sec-but | H | H | Cl | H | H | >200 | 9.5 | 20 |
| MC 913 | S | Me | H | sec-but | F | H | H | H | H | 140 | 0.41 | 341 |
| MC 918 | S | Me | H | sec-but | H | F | F | H | H | >200 | 1.2 | >166 |
| MC 919 | S | Me | H | sec-but | H | H | H | H | H | 105 | 11 | 9.5 |

TABLE 2-continued

Cytotoxicity and anti-HIV-1 Activity of MC Compounds.

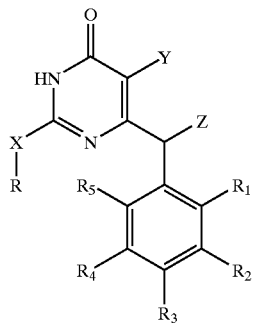

(A)

| Compd. | X | Y | Z | R | R¹ | R² | R³ | R⁴ | R⁵ | CC$_{50}$[b] [μM] | EC$_{50}$[c] [μM] | SI[d] |
|---|---|---|---|---|---|---|---|---|---|---|---|---|
| MC 912 | S | Me | H | Me | Cl | H | H | H | Cl | >200 | 3.2 | >62 |
| MC 914 | S | Me | H | iso-prop | Cl | H | H | H | Cl | >200 | 1.3 | >154 |
| MC 920 | S | Me | H | n-but | Cl | H | H | H | Cl | >200 | 1.17 | >171 |
| MC 916 | S | Me | H | iso-but | Cl | H | H | H | Cl | >200 | 1.2 | >166 |
| MC 850 | S | Me | H | sec-but | Cl | H | H | H | Cl | >200 | 0.05 | >4,000 |
| MC 915 | S | Me | H | c-pent | Cl | H | H | H | Cl | >200 | 1.8 | >111 |
| MC 917 | S | Me | H | c-hex | Cl | H | H | H | Cl | >200 | 22 | >9 |
| MC 869 | S | Me | H | Me | F | H | H | H | F | 200 | 0.19 | 1,053 |
| MC 881 | S | Me | H | iso-prop | F | H | H | H | F | >200 | 0.05 | >4,000 |
| MC 905 | S | Me | H | n-but | F | H | H | H | F | >200 | 0.08 | >2,500 |
| MC 921 | S | Me | H | iso-but | F | H | H | H | F | 64 | 0.1 | 640 |
| MC 849 | S | Me | H | sec-but | F | H | H | H | F | 80 | 0.001 | 8,000 |
| MC 922 | S | Me | H | c-pent | F | H | H | H | F | >200 | 0.08 | >2,500 |
| MC 923 | S | Me | H | c-hex | F | H | H | H | F | >200 | 0.09 | >2,222 |
| MC 1060 | S | Me | Me | Me | F | H | H | H | F | >200 | 0.04 | >5,000 |
| MC 1109 | S | Me | Me | sec-but | F | H | H | H | F | 200 | 0.03 | >6,666 |
| MC 1047 | S | Me | Me | c-pent | F | H | H | H | F | >200 | 0.009 | >22,222 |
| MC 798 | S | Et | H | sec-but | H | H | H | H | H | >200 | 1.0 | >200 |
| MC 1037 | S | Et | H | iso-prop | F | H | H | H | F | 65 | 0.2 | 326 |
| MC 1038 | S | Et | H | sec-but | F | H | H | H | F | >200 | 0.1 | >2,000 |
| MC 804 | S | Et | H | sec-but | CH=CH—CH=CH | | H | H | H | >200 | 5.3 | >34 |
| MC 1039 | S | iso-prop | H | iso-prop | F | H | H | H | F | >200 | 0.4 | >500 |
| MC 852 | S | allyl | H | sec-but | H | H | H | H | H | >200 | 3 | >67 |
| MC 856 | S | n-prop | H | sec-but | H | H | H | H | H | 190 | 12 | 16 |
| MC 834 | S | n-but | H | sec-but | H | H | H | H | H | >200 | >200 | — |
| MC 1119 | NH | H | H | ethyl | F | H | H | H | F | >200 | 0.8 | >250 |
| MC 1078 | NH | H | H | n-prop | F | H | H | H | F | 200 | 0.11 | 1,818 |
| MC 979 | NH | H | H | iso-prop | F | H | H | H | F | >200 | 0.38 | >526 |
| MC 980 | NH | H | H | c-prop | F | H | H | H | F | >200 | 3.17 | >63 |
| MC 1077 | NH | H | H | n-but | F | H | H | H | F | 100 | 0.10 | 1,000 |
| MC 945 | NH | H | H | sec-but | F | H | H | H | F | >200 | 0.13 | >1,540 |
| MC 1043 | NH | H | H | MeOethyl | F | H | H | H | F | >200 | 0.8 | >250 |
| MC 1022 | NH | H | H | c-pent | F | H | H | H | F | >200 | 0.09 | >2,222 |
| MC 1049 | NH | H | H | c-hex | F | H | H | H | F | 66 | 0.14 | 471 |
| MC 1048 | NH | H | Me | c-pent | F | H | H | H | F | 75 | 0.03 | 2,500 |
| MC 1118 | NH | Me | H | iso-prop | F | H | H | H | F | 190 | 0.03 | 6,333 |
| MC 1130 | NH | Me | H | sec-but | F | H | H | H | F | 200 | 0.07 | 2,857 |
| MC 1050 | NH | Me | H | c-pent | F | H | H | H | F | >200 | 0.02 | >10,000 |
| MC 1105 | NH | Me | H | benzyl | F | H | H | H | F | 50 | 0.50 | 100 |
| MC 1129 | NH | Me | H | c-pent | F | H | H | H | F | 90 | 0.02 | 4,500 |
| MC 1167 | NH | H | H | Me | F | H | H | H | F | >200 | 1.5 | >133 |
| MC 1168 | NH | Me | H | Me | F | H | H | H | F | 135 | 0.4 | 335 |
| MC 1186 | NH | Me | H | n-prop | F | H | H | H | F | >200 | 0.02 | >10,000 |
| MC 1185 | NH | Me | H | n-but | F | H | H | H | F | >200 | 0.02 | >10,000 |
| MC 1178 | NH | H | Me | Me | F | H | H | H | F | 106 | 0.11 | 964 |
| MC 1190 | NH | H | Me | n-prop | F | H | H | H | F | 103 | 0.02 | 5,150 |
| MC 1191 | NH | H | Me | iso-prop | F | H | H | H | F | 115 | 0.03 | 3,830 |
| MC 1189 | NH | H | Me | n-but | F | H | H | H | F | 52 | 0.03 | 1,730 |
| MC 1192 | NH | H | Me | sec-but | F | H | H | H | F | 86 | 0.04 | 2,150 |
| MC 1180 | NH | H | Me | c-hex | F | H | H | H | F | 56 | 0.02 | 2,545 |
| MC 1170 | NH | Me | Me | Me | F | H | H | H | F | 200 | 0.03 | >6,666 |
| MC 1187 | NH | Me | Me | n-but | F | H | H | H | F | 83 | 0.01 | 8,300 |
| MC 1181 | NH | Me | Me | c-hex | F | H | H | H | F | 58 | 0.03 | 2,231 |
| MC 1182 | N | H | H | Me$_2$ | F | H | H | H | F | >200 | 0.05 | >4,000 |
| MC 1183 | N | H | H | Me-piperaz | F | H | H | H | F | >200 | 7.1 | >28 |
| MC 1188 | N | H | H | morph | F | H | H | H | F | >200 | 0.6 | >333 |

TABLE 2-continued

Cytotoxicity and anti-HIV-1 Activity of MC Compounds.

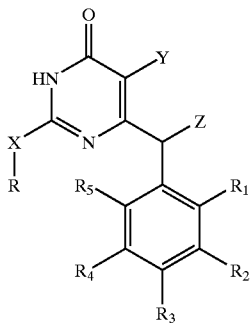

(A)

| Compd. | X | Y | Z | R | $R^1$ | $R^2$ | $R^3$ | $R^4$ | $R^5$ | $CC_{50}^{b}$ [μM] | $EC_{50}^{c}$ [μM] | $SI^{d}$ |
|---|---|---|---|---|---|---|---|---|---|---|---|---|
| MC 1193 | N | H | H | thiomorph | F | H | H | H | F | >200 | 0.05 | >4,000 |
| MC 1194 | N | H | H | piperid | F | H | H | H | F | >200 | 0.02 | >10,000 |
| MC 1196 | N | H | H | pyrrolid | F | H | H | H | F | >200 | 2.1 | >95 |
| MC 1202 | N | H | H | $Et_2$ | F | H | H | H | F | >200 | 0.26 | >769 |
| MC 1204 | N | H | H | (n-prop)$_2$ | F | H | H | H | F | >200 | 3.8 | >53 |
| MC 1195 | N | Me | H | $Me_2$ | F | H | H | H | F | >200 | 0.02 | >10,000 |
| MC 1203 | N | Me | H | Me-piperaz | F | H | H | H | F | >200 | 0.36 | >555 |
| MC 1205 | N | Me | H | morph | F | H | H | H | F | >200 | 0.047 | >4,255 |
| MC 1206 | N | Me | H | thiomorph | F | H | H | H | F | >200 | 0.09 | >2,222 |
| MC 1137 | S | Me | Me | iso-prop | F | H | H | H | F | 200 | 0.007 | 28,571 |
| MC 1175 | S | Me | Me | n-but | F | H | H | H | F | 112 | 0.008 | 14,000 |
| MC 1153 | S | Me | Me | iso-but | F | H | H | H | F | >200 | 0.01 | >20,000 |
| MC 1174 | S | Me | Me | c-hex | F | H | H | H | F | >200 | 0.018 | >11,111 |
| MC 1047+ | S | Me | Me | c-pent | F | H | H | H | F | >200 | 0.002 | >100,000 |
| MC 1047− | S | Me | Me | c-pent | F | H | H | H | F | >200 | 0.7 | >286 |
| MC 1161 | S | H | H | MeSMe | F | H | H | H | F | >200 | 0.80 | >250 |
| MC 1162 | S | Me | H | MeSMe | F | H | H | H | F | 30 | 0.12 | 250 |
| MC 1157 | S | Et | H | MeSMe | F | H | H | H | F | 50 | 0.11 | 454 |
| MC 1145 | S | iso-prop | H | MeSMe | F | H | H | H | F | 200 | 0.10 | 2,000 |
| MC 1140 | S | H | H | MeSMe | H | H | H | H | H | >200 | 20 | >10 |

[a]Data represent mean values of at least two separate experiments.
[b]Compound dose required to reduce the viability of mock-infected cells by 50%, as determined by the MMT method.
[c]Compound dose required to achieve 50% protection of MT-4 cells from HIV-1 induced cytopathogenicity, as determined by the MTT method.
[d]Selectivity index, $CC_{50}/EC_{50}$ ratio.

What is claimed is:

1. A compound of the formula:

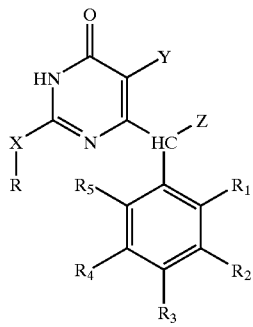

(A)

wherein:

a) X is —NK;
b) R is —$C_{1-4}$alkyl optionally substituted by one or more of heteroatoms selected from O, S, and N, —$C_{3-6}$cycloalkyl optionally substituted by one or more of heteroatoms selected from O, S, and N, -aryl, arylalkyl, or heterocycle;
c) Y is —H, —$C_{1-4}$alkyl, or —$C_{3-6}$cycloalkyl;
d) Z is —$C_{1-4}$alkyl, or —$C_{3-6}$cycloalkyl;
e) $R_1$ is —H, —$C_{1-4}$alkyl, halogen, —$NO_2$, —OW, or —SW;
f) $R_2$ is —H, —$C_{1-4}$alkyl, -halogen, —$NO_2$, —OW, or —SW;
g) $R_3$ is —H, —$C_{1-4}$alkyl, -halogen, —$NO_2$, —OW, or —SW;
h) $R_4$ is —H, —$C_{1-4}$alkyl, -halogen, —$NO_2$, —OW, or —SW;
i) $R_5$ is —H, —$C_{1-4}$alkyl, -halogen, —$NO_2$, —OW, or —SW;
j) K is —H, —$C_{1-4}$alkyl, or —$C_{3-6}$cycloalkyl; and
k) W is —H, —$CH_3$, or -aryl;

or a pharmaceutically acceptable salt thereof.

2. The compound of claim 1 wherein:

| | | | | | | |
|---|---|---|---|---|---|---|
| X = NH | Y = H | Z = $CH_3$ | R = cPe | $R_1$ = F | $R_2$ = H $R_3$ = H $R_4$ = H | $R_5$ = F; |
| X = NH | Y = $CH_3$ | Z = $CH_3$ | R = cPe | $R_1$ = F | $R_2$ = H $R_3$ = H $R_4$ = H | $R_5$ = F; |
| X = NH | Y = H | Z = $CH_3$ | R = $CH_{3R1}$ | = F | $R_2$ = H $R_3$ = H $R_4$ = H | $R_5$ = F; |
| X = NH | Y = H | Z = $CH_3$ | R = nPr | $R_1$ = F | $R_2$ = H $R_3$ = H $R_4$ = H | $R_5$ = F; |
| X = NH | Y = H | Z = $CH_3$ | R = iPr | $R_1$ = F | $R_2$ = H $R_3$ = H $R_4$ = H | $R_5$ = F; |
| X = NH | Y = H | Z = $CH_3$ | R = nBu | $R_1$ = F | $R_2$ = H $R_3$ = H $R_4$ = H | $R_5$ = F; |
| X = NH | Y = H | Z = $CH_3$ | R = sBu | $R_1$ = F | $R_2$ = H $R_3$ = H $R_4$ = H | $R_5$ = F; |
| X = NH | Y = H | Z = $CH_3$ | R = cHex | $R_1$ = F | $R_2$ = H $R_3$ = H $R_4$ = H | $R_5$ = F; |
| X = NH | Y = $CH_3$ | Z = $CH_3$ | R = $CH_3$ | $R_1$ = F | $R_2$ = H $R_3$ = H $R_4$ = H | $R_5$ = F; |
| X = NH | Y = $CH_3$ | Z = $CH_3$ | R = nBu | $R_1$ = F | $R_2$ = H $R_3$ = H $R_4$ = H | $R_5$ = F; or |
| X = NH | Y = $CH_3$ | Z = $CH_3$ | R = cHex | $R_1$ = F | $R_2$ = H $R_3$ = H $R_4$ = H | $R_5$ = F; and | further wherein cPe is cyclopentyl, nPr is n-propyl, iPr is isopropyl, nBu is n-butyl, sBu is sec-butyl, and cHex is cyclohexyl.

3. The compound of claim 1 wherein X is —NK.

4. The compound of claim 1 wherein:
a) X is —NK; and
b) K is —H or —$C_{1-4}$alkyl.

5. The compound of claim 1 wherein:
a) X is —NK;
b) R is —$C_{1-4}$alkyl or —$C_{3-6}$cycloalkyl, optionally substituted by one or more of heteroatoms selected from O, S, and N; and
c) K is —H or —$C_{1-4}$alkyl.

6. The compound of claim 1 wherein:
a) X is —NK;
b) R is —$C_{1-4}$alkyl or —$C_{3-6}$cycloalkyl; and
c) K is —H or —$C_{1-4}$alkyl.

7. The compound of claim 1 wherein:
a) X is —NK;
b) Y is —$C_{1-4}$alkyl;
c) Z is —$C_{1-4}$alkyl;
d) $R_1$ is halogen;
e) $R_2$ is —H;
f) $R_3$ is —H;
g) $R_4$ is —H; and
h) $R_5$ is -halogen.

8. The compound of claim 1 wherein:
a) X is —NK;
b) K is —H or —$C_{1-4}$alkyl;
c) Y is —$C_{1-4}$alkyl;
d) Z is —$C_{1-4}$alkyl;
e) $R_1$ is halogen;
f) $R_2$ is —H;
g) $R_3$ is —H;
h) $R_4$ is —H; and
i) $R_5$ is -halogen.

9. The compound of claim 1 wherein:
a) X is —NK;
b) R is —$C_{1-4}$alkyl or —$C_{3-6}$cycloalkyl, optionally substituted by one or more of heteroatoms selected from O, S, and N;
c) K is —H or —$C_{1-4}$alkyl;
d) Y is —$C_{1-4}$alkyl;
e) Z is —$C_{1-4}$alkyl;
f) $R_1$ is halogen;
g) $R_2$ is —H;
h) $R_3$ is —H;
i) $R_4$ is —H; and
j) $R_5$ is -halogen.

10. The compound of claim 1 wherein:
a) X is —NK;
b) R is —$C_{1-4}$alkyl or —$C_{3-6}$cycloalkyl;
c) K is —H or —$C_{1-4}$alkyl;
d) Y is —$C_{1-4}$alkyl;
e) Z is —$C_{1-4}$alkyl;
f) $R_1$ is halogen;
g) $R_2$ is —H;
h) $R_3$ is —H;
i) $R_4$ is —H; and
j) $R_5$ is -halogen.

11. The compound of claim 1 wherein X is NH, Y is $CH_3$, Z is $CH_3$, R is cyclopentyl, $R_1$ is F, $R_2$ is H, $R_3$ is H, $R_4$ is H, and $R_5$ is F.

12. A pharmaceutical composition comprising the compound of claim 1 and a pharmaceutically acceptable carrier.

13. A pharmaceutical composition comprising the compound of claim 3 and a pharmaceutically acceptable carrier.

14. A pharmaceutical composition comprising the compound of claim 11 and a pharmaceutically acceptable carrier.

15. A process for preparing a compound of claim 1 wherein X is —NK comprising reacting a S-methyl(5-alkyl)-6-benzyl(substituted)-2-thiouracil with an amine.

16. A method of treating infection by HIV or of treating AIDS, comprising administering to a mammal an effective amount of a compound of claim 1, wherein X is —NK.

17. The method of claim 16 wherein:
a) X is —NK;

b) R is —$C_{1-4}$alkyl or —$C_{3-6}$cycloalkyl; and
c) K is —H or —$C_{1-4}$alkyl.

18. The method of claim 16 wherein:
a) X is —NK;
b) R is —$C_{1-4}$alkyl or —$C_{3-6}$cycloalkyl;
c) K is —H or —$C_{1-4}$alkyl;
d) Y is —$C_{1-4}$alkyl;
e) Z is —$C_{1-4}$alkyl;
f) $R_1$ is halogen;
g) $R_2$ is —H;
h) $R_3$ is —H;
i) $R_4$ is —H; and
j) $R_5$ is -halogen.

19. A compound of the formula:

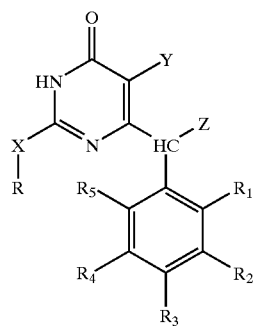

(A)

wherein:
a) X is —NK;
b) R is —$C_{1-4}$alkyl optionally substituted by one or more of heteroatoms selected from O, S, and N, —$C_{3-6}$ cycloalkyl optionally substituted by one or more of heteroatoms selected from O, S, and N, -aryl, arylalkyl, or heterocycle;
c) Y is —$C_{1-4}$alkyl, or —$C_{3-6}$cycloalkyl;
d) Z is —H, —$C_{1-4}$alkyl, or —$C_{3-6}$cycloalkyl;
e) $R_1$ is —H, —$C_{1-4}$alkyl, halogen, —$NO_2$, —OW, or —SW;
f) $R_2$ is —H, —$C_{1-4}$alkyl, -halogen, —$NO_2$, —OW, or —SW;
g) $R_3$ is —H, —$C_{1-4}$alkyl, -halogen, —$NO_2$, —OW, or —SW;
h) $R_4$ is —H, —$C_{1-4}$alkyl, -halogen, —$NO_2$, —OW, or —SW;
i) $R_5$ is —H, —$C_{1-4}$alkyl, -halogen, —$NO_2$, —OW, or —SW;
j) K is —H, —$C_{1-4}$alkyl, or —$C_{3-6}$cycloalkyl; and
k) W is —H, —$CH_3$, or -aryl;

or a pharmaceutically acceptable salt thereof.

20. The compound of claim 19 wherein:

| | | | | | | | | |
|---|---|---|---|---|---|---|---|---|
| X = NH | Y = $CH_3$ | Z = H | R = iPr | $R_1$ = F | $R_2$ = H | $R_3$ = H | $R_4$ = H | $R_5$ = F; |
| X = NH | Y = $CH_3$ | Z = H | R = sBu | $R_1$ = F | $R_2$ = H | $R_3$ = H | $R_4$ = H | $R_5$ = F; |
| X = NH | Y = $CH_3$ | Z = H | R = cPe | $R_1$ = F | $R_2$ = H | $R_3$ = H | $R_4$ = H | $R_5$ = F; |
| X = NH | Y = $CH_3$ | Z = H | R = benz | $R_1$ = F | $R_2$ = H | $R_3$ = H | $R_4$ = H | $R_5$ = F; |
| X = NH | Y = $CH_3$ | Z = H | R = $CH_3$ | $R_1$ = F | $R_2$ = H | $R_3$ = H | $R_4$ = H | $R_5$ = F; |
| X = NH | Y = $CH_3$ | Z = H | R = nPr | $R_1$ = F | $R_2$ = H | $R_3$ = H | $R_4$ = H | $R_5$ = F; |
| X = NH | Y = $CH_3$ | Z = H | R = nBu | $R_1$ = F | $R_2$ = H | $R_3$ = H | $R_4$ = H | $R_5$ = F; or |
| X = $NCH_3$ | Y = $CH_3$ | Z = H | R = $CH_3$ | $R_1$ = F | $R_2$ = H | $R_3$ = H | $R_4$ = H | $R_5$ = F; | and further wherein cPe is cyclopentyl, nPr is n-propyl, iPr is isopropyl, nBu is n-butyl, sBu is sec-butyl, and benz is benzyl.

21. A compound of the formula:

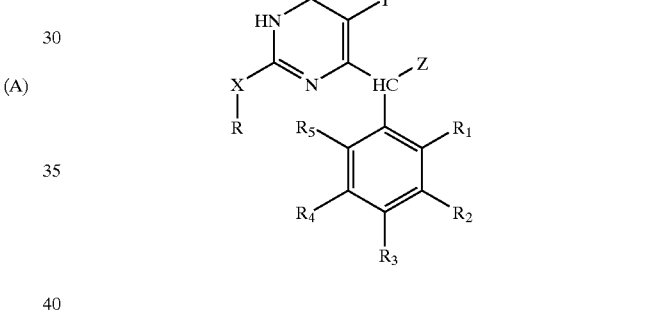

(A)

wherein:
a) X is —NK;
b) R is —$C_{1-4}$alkyl optionally substituted by one or more of heteroatoms selected from O, S, and N, —$C_{3-6}$ cycloalkyl optionally substituted by one or more of heteroatoms selected from O, S, and N, -aryl, arylalkyl, or heterocycle;
c) Y is H, —$C_{1-4}$alkyl, or —$C_{3-6}$cycloalkyl;
d) Z is —H, —$C_{1-4}$alkyl, or —$C_{3-6}$cycloalkyl;
e) $R_1$ is —$C_{1-4}$alkyl, halogen, —$NO_2$, —OW, or —SW;
f) $R_2$ is —H, —$C_{1-4}$alkyl, -halogen, —$NO_2$, —OW, or —SW;
g) $R_3$ is —H, —$C_{1-4}$alkyl, -halogen, —$NO_2$, —OW, or —SW;
h) $R_4$ is —H, —$C_{1-4}$alkyl, -halogen, —$NO_2$, —OW, or —SW;
i) $R_5$ is —H, —$C_{1-4}$alkyl, -halogen, —$NO_2$, —OW, or —SW;
j) K is —H, —$C_{1-4}$alkyl, or —$C_{3-6}$cycloalkyl; and
k) W is —H, —$CH_3$, or -aryl;

or a pharmaceutically acceptable salt thereof.

22. The compound of claim 21 wherein:

| | | | | | | | | |
|---|---|---|---|---|---|---|---|---|
| X = NH | Y = H | Z = H | R = Et | $R_1$ = F | $R_2$ = H | $R_3$ = H | $R_4$ = H | $R_5$ = F; |
| X = NH | Y = H | Z = H | R = nPr | $R_1$ = F | $R_2$ = H | $R_3$ = H | $R_4$ = H | $R_5$ = F; |
| X = NH | Y = H | Z = H | R = iPr | $R_1$ = F | $R_2$ = H | $R_3$ = H | $R_4$ = H | $R_5$ = F; |
| X = NH | Y = H | Z = H | R = cPr | $R_1$ = F | $R_2$ = H | $R_3$ = H | $R_4$ = H | $R_5$ = F; |
| X = NH | Y = H | Z = H | R = nBu | $R_1$ = F | $R_2$ = H | $R_3$ = H | $R_4$ = H | $R_5$ = F; |
| X = NH | Y = H | Z = H | R = sBu | $R_1$ = F | $R_2$ = H | $R_3$ = H | $R_4$ = H | $R_5$ = F; |
| X = NH | Y = H | Z = H | R = MeOEt | $R_1$ = F | $R_2$ = H | $R_3$ = H | $R_4$ = H | $R_5$ = F; |
| X = NH | Y = H | Z = H | R = cPe | $R_1$ = F | $R_2$ = H | $R_3$ = H | $R_4$ = H | $R_5$ = F; |
| X = NH | Y = H | Z = H | R = cHex | $R_1$ = F | $R_2$ = H | $R_3$ = H | $R_4$ = H | $R_5$ = F; |
| X = NH | Y = H | Z = H | R = $CH_3$ | $R_1$ = F | $R_2$ = H | $R_3$ = H | $R_4$ = H | $R_5$ = F; |
| X = $NCH_3$ | Y = H | Z = H | R = $CH_3$ | $R_1$ = F | $R_2$ = H | $R_3$ = H | $R_4$ = H | $R_5$ = F; |
| X = NEt | Y = H | Z = H | R = Et | $R_1$ = F | $R_2$ = H | $R_3$ = H | $R_4$ = H | $R_5$ = F; or |
| X = NnPr | Y = H | Z = H | R = nPr | $R_1$ = F | $R_2$ = H | $R_3$ = H | $R_4$ = H | $R_5$ = F; | and further wherein Et is ethyl, cPe is cyclopentyl, nPr is n-propyl, iPr is isopropyl, cPr is cyclopropyl, nBu is n-butyl, sBu is sec-butyl, and cHex is cyclohexyl.

23. A compound of the formula:

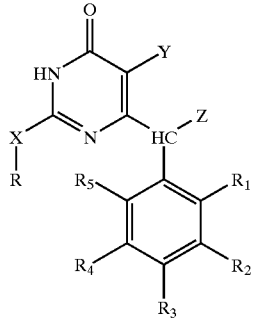

(A)

wherein:

| | | | | | | | | |
|---|---|---|---|---|---|---|---|---|
| X = N | Y = $CH_3$ | Z = H | R = Me-Pip | $R_1$ = F | $R_2$ = H | $R_3$ = H | $R_4$ = H | $R_5$ = F; |
| X = N | Y = $CH_3$ | Z = H | R = Morph | $R_1$ = F | $R_2$ = H | $R_3$ = H | $R_4$ = H | $R_5$ = F; |
| X = N | Y = $CH_3$ | Z = H | R = S-morp | $R_1$ = F | $R_2$ = H | $R_3$ = H | $R_4$ = H | $R_5$ = F; |
| X = N | Y = H | Z = H | R = Me-Pip | $R_1$ = F | $R_2$ = H | $R_3$ = H | $R_4$ = H | $R_5$ = F; |
| X = N | Y = H | Z = H | R = Morph | $R_1$ = F | $R_2$ = H | $R_3$ = H | $R_4$ = H | $R_5$ = F; |
| X = N | Y = H | Z = H | R = S-morp | $R_1$ = F | $R_2$ = H | $R_3$ = H | $R_4$ = H | $R_5$ = F; |
| X = N | Y = H | Z = H | R = Piper | $R_1$ = F | $R_2$ = H | $R_3$ = H | $R_4$ = H | $R_5$ = F; or |
| X = N | Y = H | Z = H | R = Pyrroli | $R_1$ = F | $R_2$ = H | $R_3$ = H | $R_4$ = H | $R_5$ = F, and | further wherein Me-Pip is methylpiperidinyl, Morph is morpholinyl, S-morp is thiomorpholinyl, Piper is piperidinyl, and pyrroli is pyrrolidinyl.

24. The pharmaceutical composition of claim 12 in the form of an orally-administratable tablet.

25. The pharmaceutical composition of claim 12 in the form of an orally-administratable suspension.

26. The pharmaceutical composition of claim 12 in the form of a nasal spray.

27. The pharmaceutical composition of claim 12 in the form of a sterile injectable preparation.

28. A pharmaceutical composition comprising the compound of claim 19 and a pharmaceutically acceptable carrier.

29. The pharmaceutical composition of claim 28 in the form of an orally-administratable tablet.

30. The pharmaceutical composition of claim 28 in the form of an orally-administratable suspension.

31. The pharmaceutical composition of claim 28 in the form of a nasal spray.

32. The pharmaceutical composition of claim 28 in the form of a sterile injectable preparation.

33. A pharmaceutical composition comprising the compound of claim 21 and a pharmaceutically acceptable carrier.

34. The pharmaceutical composition of claim 33 in the form of an orally-administratable tablet.

35. The pharmaceutical composition of claim 33 in the form of an orally-administratable suspension.

36. The pharmaceutical composition of claim 33 in the form of a nasal spray.

37. The pharmaceutical composition of claim 33 in the form of a sterile injectable preparation.

38. A pharmaceutical composition comprising the compound of claim 23 and a pharmaceutically acceptable carrier.

39. The pharmaceutical composition of claim 38 in the form of an orally-administratable tablet.

40. The pharmaceutical composition of claim 38 in the form of an orally-administratable suspension.

41. The pharmaceutical composition of claim 38 in the form of a nasal spray.

42. The pharmaceutical composition of claim 38 in the form of a sterile injectable preparation.

43. 2-Cyclopentylamino-6-{1-(2,6-difluorophenyl) ethyl}-3,4-dihydro-5-methylpyrimidin-4-(3H)-one.

44. A method of treating infection by HIV or of treating AIDS, comprising administering to a mammal an effective amount of a compound of claim 43.

45. A pharmaceutical composition comprising the compound of claim 43 and a pharmaceutically acceptable carrier.

46. The pharmaceutical composition of claim 45 in the form of an orally-administratable tablet.

47. The pharmaceutical composition of claim 46 in the form of an orally-administratable suspension.

48. The pharmaceutical composition of claim 46 in the form of a nasal spray.

49. The pharmaceutical composition of claim 46 in the form of a sterile injectable preparation.

* * * * *